United States Patent
Yan et al.

(10) Patent No.: US 11,403,493 B2
(45) Date of Patent: Aug. 2, 2022

(54) DEVICE AND METHOD FOR UNIVERSAL LESION DETECTION IN MEDICAL IMAGES

(71) Applicant: Ping An Technology (Shenzhen) Co., Ltd., Shenzhen (CN)

(72) Inventors: Ke Yan, Bethesda, MD (US); Jinzheng Cai, Bethesda, MD (US); Adam P Harrison, Bethesda, MD (US); Dakai Jin, Bethesda, MD (US); Le Lu, Bethesda, MD (US)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 256 days.

(21) Appl. No.: 16/983,373

(22) Filed: Aug. 3, 2020

(65) Prior Publication Data

US 2021/0224603 A1 Jul. 22, 2021

Related U.S. Application Data

(60) Provisional application No. 62/962,271, filed on Jan. 17, 2020.

(51) Int. Cl.
*G06K 9/00* (2022.01)
*G06K 9/62* (2022.01)
(Continued)

(52) U.S. Cl.
CPC ........... *G06K 9/6259* (2013.01); *G06K 9/628* (2013.01); *G06K 9/6292* (2013.01);
(Continued)

(58) Field of Classification Search
CPC .... G06K 9/6259; G06K 9/628; G06K 9/6292; G06K 9/6224; G16H 50/20; G16H 30/40; G06V 10/255; G06V 2201/03; G06V 2201/032; G06V 20/695; G06V 40/162; G06V 20/80; G06V 20/698; G06N 3/0454; G06N 3/08; G06N 20/20; G06T 7/0012; G06T 2207/20081; G06T 2207/30056; G06T 2207/30096; G06T 2207/30064;
(Continued)

(56) References Cited

U.S. PATENT DOCUMENTS

| | | | |
|---|---|---|---|
| 2011/0007954 A1* | 1/2011 | Suehling | G06V 40/10 382/128 |
| 2021/0225511 A1* | 7/2021 | Kiraly | G06K 9/6292 |
| 2022/0180514 A1* | 6/2022 | Vlasimsky | G06V 10/764 |

* cited by examiner

*Primary Examiner* — Atiba O Fitzpatrick
(74) *Attorney, Agent, or Firm* — Anova Law Group, PLLC

(57) ABSTRACT

A method for performing a computer-aided diagnosis (CAD) for universal lesion detection includes: receiving a medical image; processing the medical image to predict lesion proposals and generating cropped feature maps corresponding to the lesion proposals; for each lesion proposal, applying a plurality of lesion detection classifiers to generate a plurality of lesion detection scores, the plurality of lesion detection classifiers including a whole-body classifier and one or more organ-specific classifiers; for each lesion proposal, applying an organ-gating classifier to generate a plurality of weighting coefficients corresponding to the plurality of lesion detection classifiers; and for each lesion proposal, performing weight gating on the plurality of lesion detection scores with the plurality of weighting coefficients to generate a comprehensive lesion detection score.

20 Claims, 14 Drawing Sheets

(51) Int. Cl.
  *G06T 7/00*   (2017.01)
  *G16H 50/20*   (2018.01)
  *G06N 3/08*   (2006.01)
  *G06N 3/04*   (2006.01)
  *G16H 30/40*   (2018.01)
  *G06V 10/20*   (2022.01)
(52) U.S. Cl.
  CPC ............. *G06N 3/0454* (2013.01); *G06N 3/08* (2013.01); *G06T 7/0012* (2013.01); *G06V 10/255* (2022.01); *G16H 30/40* (2018.01); *G16H 50/20* (2018.01); *G06T 2207/20081* (2013.01); *G06T 2207/30056* (2013.01); *G06T 2207/30061* (2013.01); *G06T 2207/30096* (2013.01); *G06V 2201/03* (2022.01)
(58) Field of Classification Search
  CPC ..... G06T 7/10–194; G06T 2207/20112; G06T 2207/10072–10136; G06T 2207/30008–30016; G06T 2207/30028–30061; G06T 2207/30068; G06T 2207/30076–30092; G06T 2207/30101–30104; A61B 8/085; A61B 5/7485
  See application file for complete search history.

DEVICE AND METHOD FOR UNIVERSAL LESION DETECTION IN MEDICAL IMAGES

CROSS-REFERENCE TO RELATED APPLICATION

This application claims the priority of U. S. Provisional Patent Application No. 62,962,271, filed on Jan. 17, 2020, the entire contents of which are incorporated herein by reference.

TECHNICAL FIELD

The present disclosure relates to the technical field of computer-aided diagnosis (CAD) and, in particular, to a device and method for computer-aided diagnosis (CAD) for universal lesion detection in medical images.

BACKGROUND

Detection of abnormal tissues or lesions is a critical component of radiology workflows. It is time-consuming to scan through a three-dimensional (3D) medical image, spurring research on automated lesion detection to decrease reading time and improve accuracy. Existing methods generally focus on lesions of specific types in specific organs. For example, automated detections of lung nodules, liver tumors, and lymph nodes have been extensively studied. However, while some common lesion types have received much attention, many clinically significant types have been overlooked. It is also inefficient to deploy many models in practical use, with each model trained to detect one lesion type. Therefore, a universal lesion detector, which can identify a variety of lesions in the whole body, is welcome.

Universal lesion detection is highly challenging due to the great variance across lesion types and the subtle differences between lesions and non-lesions. Certain approaches have improved detection accuracy by using 3D context information or attention mechanisms. Nevertheless, there are still open issues on this task. For example, existing works may treat all lesion types as one class and use a binary classifier to predict if a box proposal is a lesion or not. Given the variance across lesion types, it is likely that some degree of parameter separation for different lesion types or different organs may be beneficial. Additionally, in available universal datasets such as DeepLesion, lesions are only annotated on part of the 2D image slices and there are missing annotations, which will undermine both training and evaluation. Further, although certain other public lesion datasets only contain annotations of single lesion types, these other public lesion datasets may still be helpful. It may be beneficial to explore their synergy with universal datasets such as DeepLesion to improve accuracy of universal lesion detection.

SUMMARY

In one aspect of the present disclosure, a method for performing a computer-aided diagnosis (CAD) for universal lesion detection is provided. The method includes: receiving a medical image; processing the medical image to predict lesion proposals and generating cropped feature maps corresponding to the lesion proposals; for each lesion proposal, applying a plurality of lesion detection classifiers to generate a plurality of lesion detection scores, the plurality of lesion detection classifiers including a whole-body classifier and one or more organ-specific classifiers; for each lesion proposal, applying an organ-gating classifier to generate a plurality of weighting coefficients corresponding to the plurality of lesion detection classifiers; and for each lesion proposal, performing weight gating on the plurality of lesion detection scores with the plurality of weighting coefficients to generate a comprehensive lesion detection score.

According to certain embodiments, processing the medical image to predict the lesion proposals and generating cropped feature maps includes: processing the medical image with a 2.5-dimensional (2.5D) feature pyramid network (FPN) to generate a feature map; processing the generated feature map with a region proposal network (RPN) to predict the lesion proposals; and for each lesion proposal, applying a region-of-interest alignment (RolAlign) layer to generate a cropped feature map corresponding to the lesion proposal.

According to certain embodiments, the lesion proposals include bounding boxes marking locations and spans of predicted lesions.

According to certain embodiments, the method further includes: applying a mask classifier to predict segmentation masks for the lesion proposals; and applying bounding-box regression on the whole-body lesion classifier to refine the bounding boxes of the lesion proposals.

According to certain embodiments, the organ-specific classifiers include one or more of: a classifier for detecting liver lesions; a classifier for detecting lung lesions; and a classifier for detecting lymph node lesions.

According to certain embodiments, the method further includes: receiving training images from a plurality of training datasets; training the organ-gating classifier using the training images and corresponding lesion annotations; performing joint training using the plurality of training datasets to generate parameters for feature extraction layers and fully-connected layers of the lesion detection classifiers; and training last layers of the lesion detection classifiers to generate a plurality of dataset experts, each dataset expert corresponding to one of the training datasets.

According to certain embodiments, the plurality of training datasets include a universal image dataset and one or more single-type image datasets, the universal image dataset containing annotations for a variety of organ and lesion types, and each single-type image dataset containing annotations for a single type of lesions.

According to certain embodiments, the single-type image datasets include one or more of: a liver lesion image dataset; a lung lesion image dataset; and a lymph-node lesion image dataset.

According to certain embodiments, the method further includes: training the lesion detection classifiers using annotated key image slices of the universal dataset and image slices of single-type datasets; applying the trained lesion detection classifiers on all slices of the universal image dataset to predict a plurality of groups of lesion proposals, each group of lesion proposals corresponding to one of the dataset experts; selecting lesion proposals with detection scores greater than a detection score threshold as positive proposals; identifying consensus proposals between positive proposals generated using the universal data expert and positive proposals generated using one of the single-type data experts; and finetuning the lesion detection classifiers using non-key image slices in the universal image dataset as negatives while ignoring the identified consensus proposals.

According to certain embodiments, identifying consensus proposals includes:

calculating an intersection over union (IoU) between a first positive proposal generated using the universal data expert and a second positive proposal generated using one of the single-type data experts; and in response to the calculated IoU being greater than an IoU threshold, identifying the first positive proposal being a consensus proposal.

According to certain embodiments, the method further includes: training the lesion detection classifiers using annotated key image slices of one or more of the training datasets; applying the trained lesion detection classifiers on non-key image slices of the one or more of the training datasets to generate a plurality of lesion proposals; establishing a corresponding relationship between the plurality of lesion proposals with existing annotations; mining lesions in the non-key image slices according to the corresponding relationship; and finetuning the lesion detection classifiers by incorporating positive proposals corresponding to the lesions mined in the un-annotated non-key image slices.

According to certain embodiments, mining lesions in the non-key image slices includes, for each lesion proposal: calculating an L2 distance from the lesion proposal to each of the existing annotations within a same patient; and in response to the L2 distance between the lesion proposal and one of the existing annotations within the same patient being below a distance threshold value, identifying the lesion proposal and the existing annotation as a positive pair, and identifying the lesion proposal as a positive proposal.

In another aspect of the present disclosure, a device for performing computer-aided diagnosis (CAD) based on a medical image for universal lesion detection is provided. The device includes: a memory, storing computer-executable instructions; and a processor, coupled with the memory and, when the computer-executable instructions being executed, configured to: receive a medical image; process the medical image to predict lesion proposals and generate cropped feature maps corresponding to the lesion proposals; for each lesion proposal, apply a plurality of lesion detection classifiers to generate a plurality of lesion detection scores, the lesion detection classifiers including a whole-body classifier and one or more organ-specific classifiers; for each lesion proposal, apply an organ-gating classifier to generate a plurality of weighting coefficients corresponding to the lesion detection classifiers; and for each lesion proposal, perform weight gating on the lesion detection scores with the weighting coefficients to generate a comprehensive lesion detection score.

According to certain embodiments, the processor is further configured to: receive training images from a plurality of training datasets; train the organ-gating classifier using the training images and corresponding lesion annotations; perform joint training using the plurality of training datasets to generate parameters for feature extraction layers and connected layers of the lesion detection classifiers; and train last layers of the lesion detection classifiers to generate a plurality of dataset experts, each dataset expert corresponding to one of the training datasets.

According to certain embodiments, the plurality of training datasets include a universal image dataset and one or more single-type image datasets, the universal image dataset containing annotations for a variety of organ and lesion types, and each single-type image dataset containing annotations for a single type of lesions.

According to certain embodiments, the processor is further configured to: train the lesion detection classifiers using annotated key image slices of the universal dataset and image slices of single-type datasets; apply the trained lesion detection classifiers on all slices of the universal image dataset to predict a plurality of groups of lesion proposals, each group of lesion proposals corresponding to one of the dataset experts; select lesion proposals with detection scores greater than a detection score threshold as positive proposals; identify consensus proposals between positive proposals generated using the universal data expert and positive proposals generated using one of the single-type data experts; and finetune the lesion detection classifiers using non-key image slices in the universal image dataset as negatives while ignoring the identified consensus proposals.

According to certain embodiments, the processor is further configured to: calculate an intersection over union (IoU) between a first positive proposal generated using the universal data expert and a second positive proposal generated using one of the single-type data experts; and in response to the calculated IoU being greater than an IoU threshold, identify the first positive proposal being a consensus proposal.

According to certain embodiments, the processor is further configured to: train the lesion detection classifiers using annotated key image slices of one or more of the training datasets; apply the trained lesion detection classifiers on non-key image slices of the one or more of the training datasets to generate a plurality of lesion proposals; establish a corresponding relationship between the plurality of lesion proposals with existing annotations; mine lesions in the non-key image slices in the one or more of the training datasets according to the corresponding relationship; and finetune the lesion detection classifiers by incorporating positive proposals corresponding to the lesions mined in the un-annotated non-key image slices.

In another aspect of the present disclosure, a non-transitory computer-readable storage medium is disclosed. The non-transitory computer-readable storage medium stores a plurality of instructions, wherein when the plurality of instructions are executed by a processor, cause the processor to: receive the medical image as an input; process the medical image to predict lesion proposals and generate cropped feature maps corresponding to the lesion proposals; for each lesion proposal, apply a plurality of lesion detection classifiers to generate a plurality of lesion detection scores, the lesion detection classifiers including a whole-body classifier and one or more organ-specific classifiers; for each lesion proposal, apply an organ-gating classifier to generate a plurality of weighting coefficients corresponding to the lesion detection classifiers; and for each lesion proposal, perform weight gating on the lesion detection scores with the weighting coefficients to generate a comprehensive lesion detection score.

According to certain embodiments, the plurality of instructions further cause the processor to: receive training images from a plurality of training datasets; train the organ-gating classifier using the training images and corresponding lesion annotations; perform joint training using the plurality of training datasets to generate parameters for feature extraction layers and connected layers of the lesion detection classifiers; and train last layers of the lesion detection classifiers to generate a plurality of dataset experts, each dataset expert corresponding to one of the training datasets.

According to certain embodiments, the plurality of training datasets include a universal image dataset and one or more single-type image datasets, the universal image dataset containing annotations for a variety of organ and lesion types, and each single-type image dataset containing annotations for a single type of lesions.

According to certain embodiments, the plurality of instructions further cause the processor to: train the lesion detection classifiers using annotated key image slices of the universal dataset and image slices of single-type datasets;

apply the trained lesion detection classifiers on all slices of the universal image dataset to predict a plurality of groups of lesion proposals, each group of lesion proposals corresponding to one of the dataset experts; select lesion proposals with detection scores greater than a detection score threshold as positive proposals; identify consensus proposals between positive proposals generated using the universal data expert and positive proposals generated using one of the single-type data experts; and finetune the lesion detection classifiers using non-key image slices in the universal image dataset as negatives while ignoring the identified consensus proposals.

According to certain embodiments, the plurality of instructions further cause the processor to: calculate an intersection over union (IoU) between a first positive proposal generated using the universal data expert and a second positive proposal generated using one of the single-type data experts; and in response to the calculated IoU being greater than an IoU threshold, identify the first positive proposal being a consensus proposal.

According to certain embodiments, the plurality of instructions further cause the processor to: train the lesion detection classifiers using annotated key image slices of one or more of the training datasets; apply the trained lesion detection classifiers on non-key image slices of the one or more of the training datasets to generate a plurality of lesion proposals; establish a corresponding relationship between the plurality of lesion proposals with existing annotations; mine lesions in the non-key image slices in the one or more of the training datasets according to the corresponding relationship; and finetune the lesion detection classifiers by incorporating positive proposals corresponding to the lesions mined in the un-annotated non-key image slices.

BRIEF DESCRIPTION OF THE DRAWINGS

In order to more clearly illustrate the technical solutions according to the embodiments of the present disclosure, the drawings used in the description of the embodiments will be briefly described below. It is obvious that the drawings in the following description are only some embodiments of the present disclosure. Other drawings may be obtained by those of ordinary skill in the art based on these drawings.

DETAILED DESCRIPTION

The technical solutions according to the embodiments of the present disclosure are described in the following with reference to the accompanying drawings. The described embodiments are only part of the embodiments of the present disclosure, but not all the embodiments. All other embodiments obtained by a person of ordinary skill in the art based on the embodiments of the present disclosure without creative efforts are within the scope of the present disclosure.

The present disclosure provides a device and method for computer-aided diagnosis (CAD) based on medical images. The CAD device and method provided in the present disclosure may be applied in automatically detecting lesions from medical images, such as from 3D computer tomography (CT) or magnetic resonance (MR) images of a patient. For example, the disclosed CAD device and method may be configured to detect multiple types of lesions from multiple organs in a 3D medical image containing whole-body, multi-organ, or single-organ anatomies.

Various CAD systems and methods have been developed for lesion detection. However, there are aspects for improvement in universal lesion detection. For example, existing works may treat all lesion types as one class and use a binary classifier to predict if a box proposal is a lesion or not. Given the variance across lesion types, it is likely that some degree of parameter separation for different lesion types or organs may be beneficial. Additionally, in available universal datasets such as DeepLesion, lesions were only annotated on some of the 2D image slices and there are missing annotations (lesions without boxes), which will undermine both training and evaluation. Further, although certain other public lesion datasets may only contain annotations of single lesion types, they may be still helpful. It may be beneficial to explore their synergy with universal datasets such as DeepLesion to improve universal lesion detection. The CAD device and method provided in the present disclosure are in part aimed to address these open issues.

Figure 1:
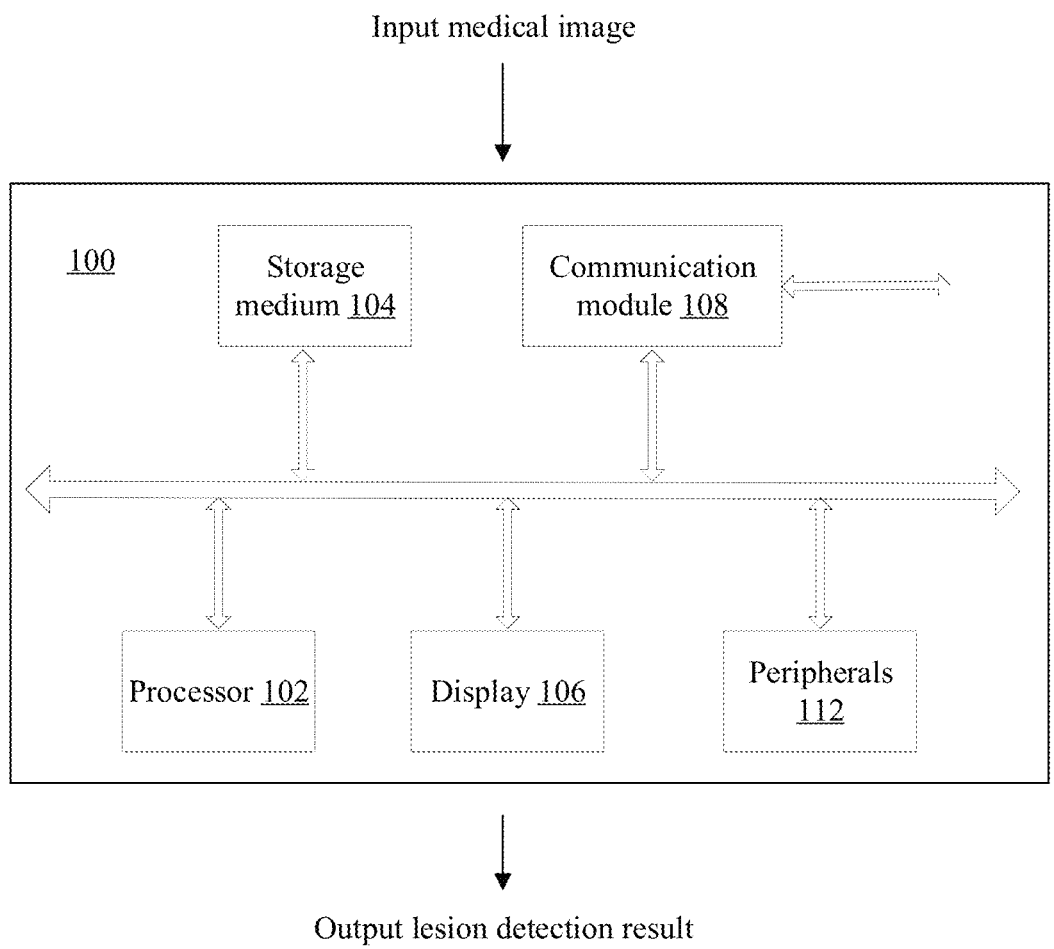
FIG. 1 illustrates a CAD device for universal lesion detection in medical images according to certain embodiments of the present disclosure.

FIG. 1 illustrates a CAD device 100 for universal lesion detection in medical images according to certain embodiments of the present disclosure. As shown in FIG. 1, the CAD device 100 may be configured to receive a medical image containing anatomical structures. In certain embodiment, the received medical image may be a 3D medical image, such as a 3D CT scan image. The medical image may be obtained from an imaging instrument, loaded from a memory module, or otherwise provided to the CAD device. The CAD device 100 may be configured to perform a neural network processing to identify and locate one or more lesions, such as tumors, from the medical image, and generate an output to provide lesion detection information. In certain embodiments, the lesion detection result may include bounding boxes marking detected lesions that overlay on the medical image to mark the lesion presence, location, and span. A detection score may also be outputted for each bounding box to signify a confidence of the marked region being a true lesion. Parameters of the neural network may be generated by a training process configured to receive training data containing a plurality of annotated medical images. In certain embodiments, the training data may include medical images from multiple datasets.

In some embodiments, the CAD device 100 may be a computing device including a processor 102 and a storage medium 104. The CAD device 100 may further include a display 106, a communication module 108, and additional peripheral devices 112. Certain devices may be omitted and other devices may be included. Processor 102 may include any appropriate processor(s). In certain embodiments, processor 102 may include multiple cores for multi-thread or parallel processing. Processor 102 may execute sequences of computer program instructions to perform various processes, such as a neural network processing program. Storage medium 104 may be a non-transitory computer-readable storage medium, and may include memory modules, such as ROM, RAM, flash memory modules, and erasable and rewritable memory, and mass storages, such as CD-ROM, U-disk, and hard disk, etc. Storage medium 104 may store computer programs and instructions for implementing various processes, when executed by processor 102, cause the processor to perform various steps of the neural network processing program of a CAD method for detecting and locating anatomical abnormalities from a medical image. The communication module 108 may include network devices for establishing connections through a network. Display 106 may include any appropriate type of computer display device or electronic device display (e.g., CRT or LCD based devices, touch screens). Peripherals 112 may include additional I/O devices, such as a keyboard, a mouse, and so on. The processor 102 may be configured to execute instructions stored on the storage medium 104 and perform various operations related to the CAD method as detailed in the following descriptions.

Figure 2:
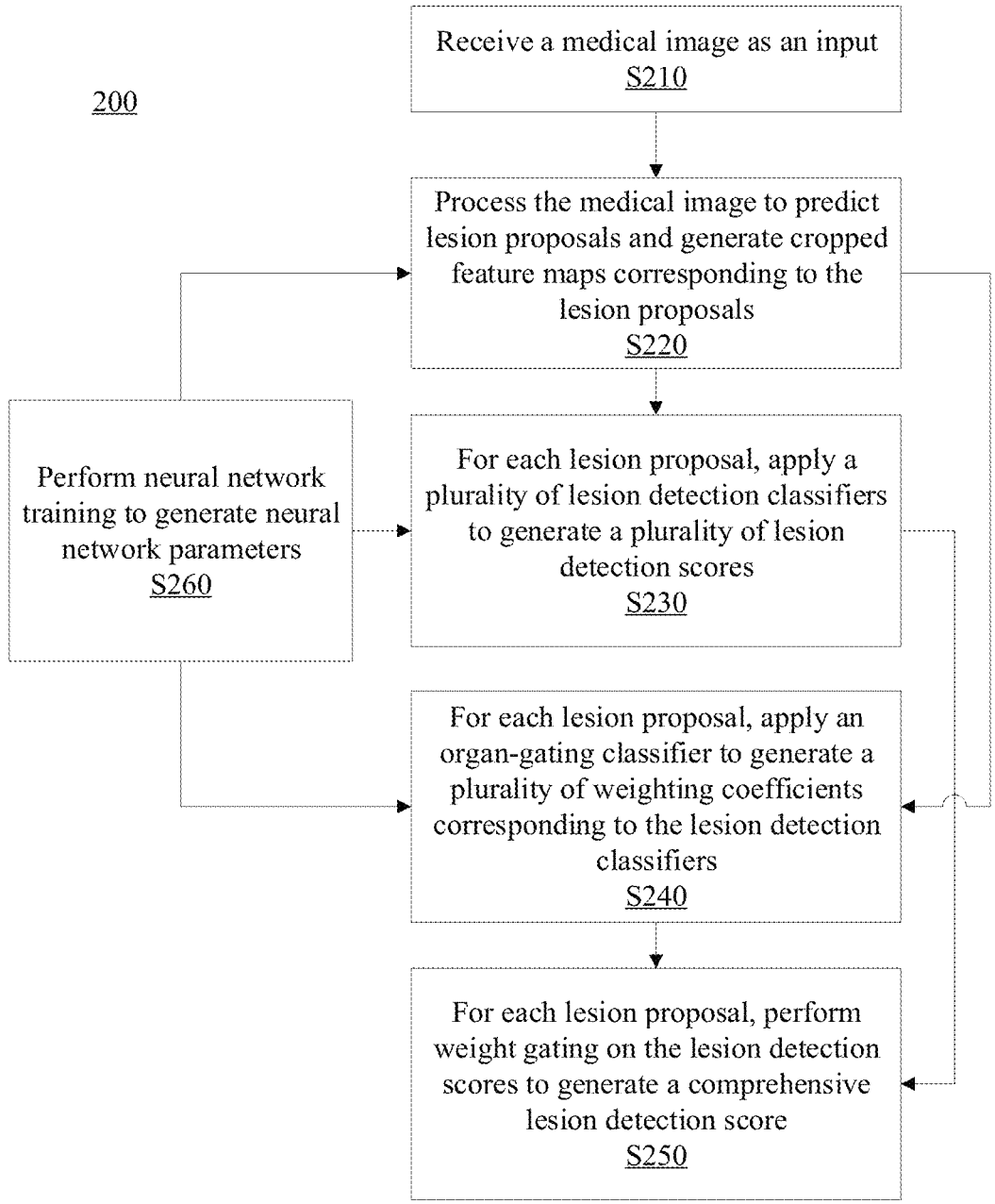
FIG. 2 illustrates a CAD method for universal lesion detection in a medical image according to some embodiments of the present disclosure.
Figure 6A:
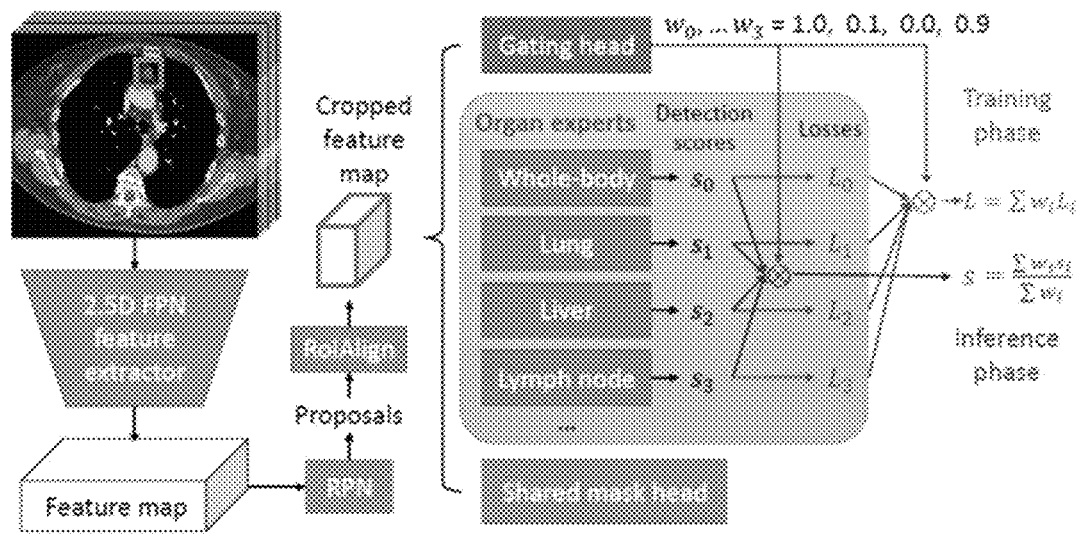
FIG. 6A illustrates exemplary aspects of the CAD universal lesion detection method according to some embodiments of the present disclosure.

FIG. 2 illustrates a CAD method 200 for universal lesion detection from a medical image according to some embodiments of the present disclosure. FIG. 6A illustrates exemplary aspects of the CAD method 200 according to some embodiments. As shown in FIG. 2, the CAD universal lesion detection method 200 may include the following exemplary steps.

In S210, an input image is received. The input image may include a medical image. The medical image may include one or more of CT scans, Mills, PET scans, etc. In an exemplary embodiment, the medical image may be a 3D image including multiple two-dimensional (2D) image slices, as shown in FIG.6A. The medical image may be generated by an imaging instrument, loaded from a memory module, or otherwise provided as an input image for process according to the disclosed CAD universal lesion detection method. The 3D image may be processed to detect and locate one or more lesions in the 3D image.

Referring back to FIG. 2, Step S220 is to process the medical image to predict lesion proposals and generate cropped feature maps corresponding to the lesion proposals. In certain embodiments, prior to performing organ-specific detections, an overall neural network processing may be performed to extract features from the input image and generate lesion proposals. As shown in FIG. 6A, in certain embodiments, the overall processing may include: processing the input image with a 2.5-dimensional (2.5D) feature pyramid network (FPN) to generate a feature map, processing the generated feature map with a region proposal network (RPN) to predict lesion proposals, and applying a region-of-interest alignment (RolAlign) layer to generate a cropped feature map for each lesion proposal.

According to certain embodiments, the CAD method may adopt a 2.5D FPN to extract features from the input image. Although 2D network structures are more efficient to compute, 3D context information in neighboring slices may be important for detection, as lesions may be less distinguishable in just one 2D slice. Thus, a 2.5D approach with 2D network structure and multi-slice image inputs may be used, taking into 3D context information while maintaining relatively low computation burden.

In certain embodiments, in order to generate lesion proposals, i.e., proposals for regions where a lesion is present, an RPN may be used to process the feature map outputted by the 2.5D FPN. The RPN may output a plurality of bounding boxes as lesion proposals to mark the presences, locations, and spans of possible lesions. Further, an RolAlign layer may be applied to align spatial locations of inputs and outputs, and generate a cropped feature map for each lesion proposal. Thus, Step 220 may output a plurality of lesion proposals as bounding boxes and cropped feature maps corresponding to the lesion proposals. Each lesion proposal may correspond to a bounding box signifying a position and span of a proposed lesion and a cropped feature map.

Referring back to FIG. 2, Step S230 of the CAD method is to apply a plurality of lesion detection classifiers to generate a plurality of lesion detection scores for each lesion proposal. In certain embodiments, the lesion detection classifiers may include a plurality of organ-specific classifiers and a whole-body classifier.

Universal lesion detection algorithms usually treat all types of lesions as one class and use a binary classifier to distinguish them from non-lesions. However, lesions in different organs may have very distinct appearances. Intuitively, training and using several classifiers corresponding to different organs and/or lesion types may be beneficial. Each classifier may learn organ-specific parameters to model the subtle difference between lesions and non-lesions of that organ and reduce the within-class variance. Therefore, the present disclosure provides an approach with organ-specific classifiers. These organ-specific classifiers may be termed as organ experts because each organ-specific classifier is specialized in detecting a specific type of lesions or lesions in a specific organ.

Figure 3:
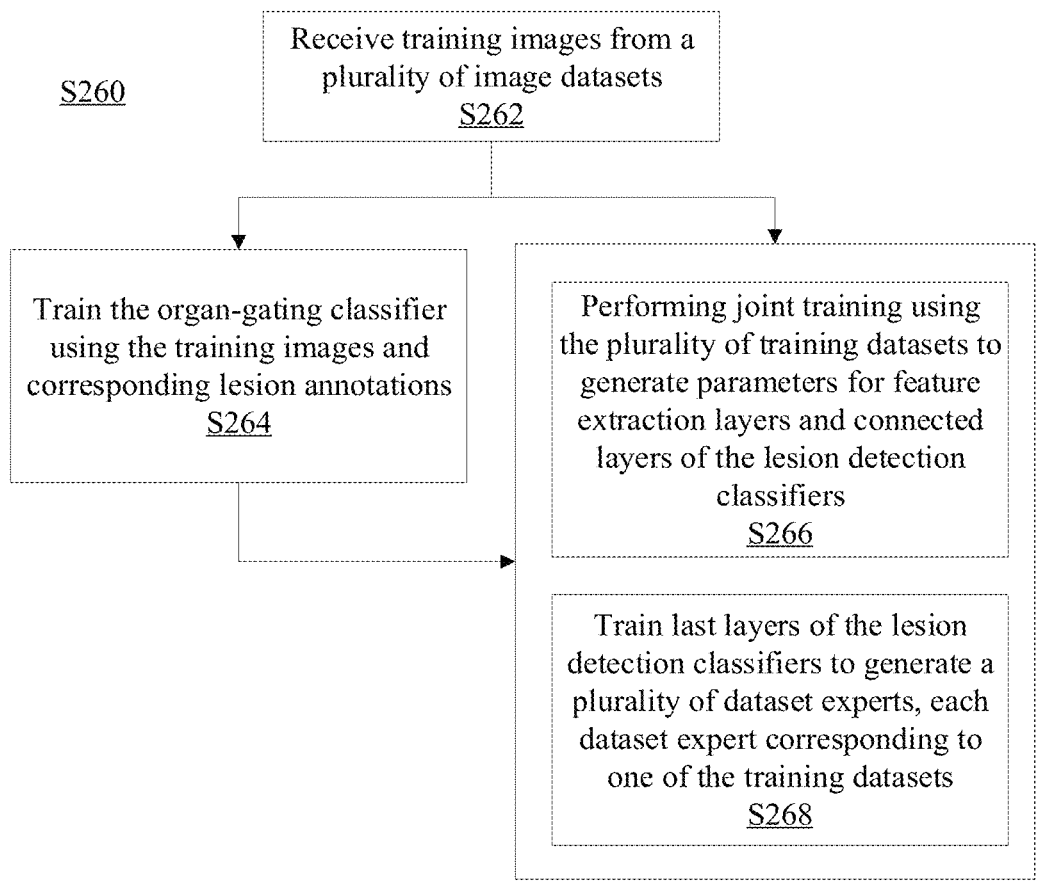
FIG. 3 illustrates steps in the training process according to certain embodiments of the present disclosure.

An example of applying the organ experts is illustrated in FIG. 3. According to certain embodiments, M organs may be chosen for the organ experts. The M organs may include major organs such as lung, liver, and lymph node, for M organ-specific classifiers. The number and types of organs are not limited in this disclosure and may be chosen according to the application and available training datasets. To cover other organs that are not included in the M organ-specific classifiers, another classifier for the whole-body may be included serving as a generalist. Each of the M organ-specific classifiers may be a classifier to differentiate lesions and non-lesions in that organ. The whole-body classifier may be a classifier to differentiate lesions and non-lesions in the whole body.

According to certain embodiments, for each lesion proposal with the corresponding bounding box and cropped feature map, each organ-specific classifier may process the lesion proposal and output a detection score for that organ and that specific lesion proposal. For example, for a lesion proposal with a corresponding cropped feature map, the $i^{th}$ organ-specific classifier may output a detection score $s_i$ for a specific lesion proposal, where i=1, . . . , M. That is, the M organ-specific classifiers may output M detection scores $S_1, \ldots S_M$ for a specific lesion proposal. The detection score $s_i$ may represent a predicted probability for the lesion proposal to correspond to a true lesion in the input image. For example, a greater value of detection score $s_i$ may signify a higher probability of the lesion proposal to be a true lesion in the $i^{th}$ organ as predicted by the organ-specific classifier. Similarly, the whole-body classifier may process each lesion proposal and output a detection score $s_0$ for that specific lesion proposal for the whole body. A greater value of the whole-body detection score $s_0$ may signify a higher probability of the lesion proposal to correspond to a true lesion in the whole body as predicted by the whole-body classifier.

Referring back to FIG. 2, Step S240 of the CAD method is to apply an organ-gating classifier to generate a plurality of weighting coefficients corresponding to the lesion detection classifiers for each lesion proposal. The organ-gating classifier is shown in FIG. 6A as the "gating head". The organ-gating classifier may be applied to the lesion proposal and corresponding cropped feature map to generate the weighting coefficients. The weighting coefficients may include a plurality of organ-specific weighting coefficients and a whole-body coefficient. For example, for the $i^{th}$ organ, a weighting coefficient $\omega_i$ may be generated to represent how much a proposal is predicted to belong to the $i^{th}$ organ, where $\omega_i \in [0, 1]$, i=1, . . . , M. A coefficient $\omega_0$=1 may also be assigned to the whole-body classifier as it corresponds to the whole body. Thus, a plurality of weighting coefficients may be expressed as $\omega_i \in [0,1]$, i=0, . . . , M.

Step S250 of the CAD method is to perform weight gating on the plurality of detection scores to generate a comprehensive detection score for each lesion proposal. In certain embodiments, for each lesion proposal, a comprehensive detection score s may be calculated as a normalized weighted sum of the plurality of detection scores using the plurality of weighting coefficients, i.e., $$s = \frac{\sum_{i=0}^{M} w_i s_i}{\sum_{i=0}^{M} w_i}. \tag{1}$$

The comprehensive detection score s may represent a comprehensive probability that a specific lesion proposal corresponds to a true lesion when taking into account all the organ-specific classifiers and the whole-body classifier. As an example, when a proposal corresponds to a lymph node (LN) near lung, the predicted organ weights may be non-zero in both LN and lung. Thus, both the organ-specific lesion detection classifiers and the whole-body lesion detection classifier may receive losses, making the organ experts overlap in their specialties, which may increase the overall generalization ability.

Comprehensive detection scores corresponding to all lesion proposals may be used to determine which ones of the lesion proposals, if any, likely correspond to true lesions as predicted by the organ-specific classifiers and the whole-body classifier. A detection score cut-off threshold a may be chosen on the receiver operating characteristic (ROC) curve according to desired sensitivity and specificity for a specific application. A lesion proposal with detection score s>σ may be kept as positive proposal as identified by the classifiers and the weighting coefficients.

In certain embodiments, the CAD method may further include applying a mask classifier to predict segmentation masks for the lesion proposals (shown as the mask head in FIG. 6A). The mask classifier may be shared by the organ experts and the whole-body classifier. In certain embodiments, bounding-box regression may be applied on the whole-body classifier to refine the bounding boxes of the lesion proposals.

The above steps of the CAD method may detect lesions in the input medical image by taking into account all the organ-specific classifiers and the whole-body classifier. The corresponding neural networks may be termed as a multi-expert lesion detector (MELD) because they take advantage of multiple organ experts, each focusing on lesions in one major organ.

The CAD method may further include a process to train the MELD using training data. As shown in FIG. 2, the CAD may include Step 260 to perform neural network training to generate neural network parameters. The network training may be performed using training data having corresponding ground-truth annotations. In certain embodiments, the neural network parameters obtained by the training process may include parameters for each stage of the neural network processing, such as the 2.5D FPN, the RPN, the RoIAlign layer, the organ-specific and whole-body classifiers, the organ-gating classifier, the mask classifier, and the bounding-box regression layer. These neural network parameters obtained by the training process are used by the MELD to detect and locate lesions in the input medical image.

Figure 6B:
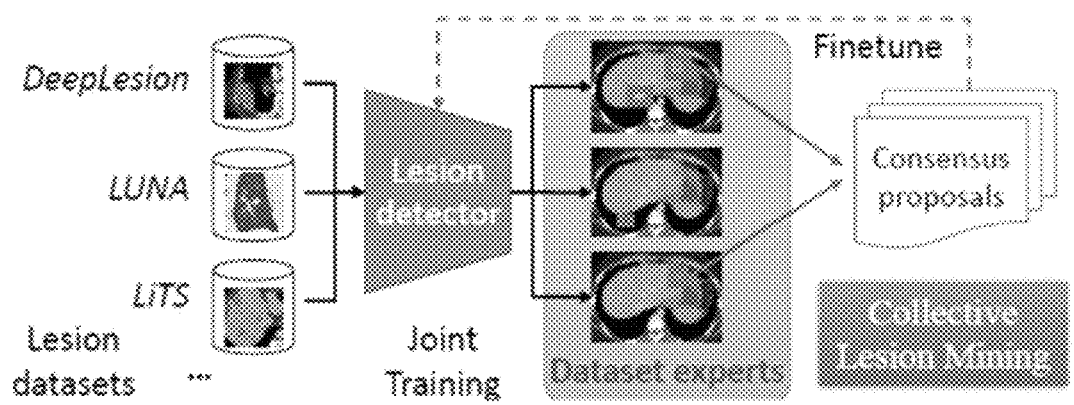
FIG. 6B illustrates exemplary aspects of the CAD universal lesion detection method according to some embodiments of the present disclosure.

FIG. 3 illustrates steps in the training process according to certain embodiments. The training process may include the following steps. Certain aspects of the training process are also illustrated in FIG. 6A and FIG. 6B.

As shown in FIG. 3, Step 262 of the training process is to receive training images from a plurality of training datasets. In order to fully utilize available annotated medical image datasets, in certain embodiments of the CAD method, a plurality of datasets may be used to train the MELD networks. As shown in FIG. 6B, These training datasets may include universal image datasets that contain a variety of organ and lesion types, such as DeepLesion, which contains over 32,000 annotated lesions identified on CT images with diverse types of radiology findings from across the body, such as lung nodules, liver tumors, enlarged lymph nodes, and so on. The training datasets may also include lesion datasets that only contain annotations of single lesion types, such as the Lung Nodule Analysis (LUNA) dataset, the Liver Tumor Segmentation Benchmark (LiTS) dataset, the NIH-Lymph Node (NIH-LN) dataset, and so on. The synergy between universal datasets and single-lesion datasets may be fully explored by incorporating both types of datasets for training the MELD to improve universal lesion detection.

Referring back to FIG. 3, Step 264 of the training process is to train the organ-gating classifier using the training images and ground-truth lesion annotations of the training datasets. According to certain embodiments, lesion and/or organ type information is included in the ground-truth annotation data. This information may be used to train the organ-gating classifier for generating weighting coefficients corresponding to the different organ experts in the MELD. For example, for training images in the DeepLesion dataset, the lesion annotation network (LesaNet) may be utilized. LesaNet was trained on lesion annotations mined from radiological reports of DeepLesion. For the purpose of providing ground-truth annotations for lesion types, LesaNet may be used to output annotations corresponding to the M organs of interest in the present disclosure. Specifically, LesaNet may be used to predict annotations of ground-truth lesion types in DeepLesion, then the predictions scores (0~1) may be adopted as soft targets to train the organ-gating classifier with a multi-label cross-entropy loss. In certain embodiments, single-type datasets may also be used for training the organ-gating classifier. In this case, the ground-truth lesion type may be determined by the specific dataset. For example, for training images from the LUNA dataset, the ground-truth lesion type may be identified as lung nodule.

As shown in FIG. 3, the training images and the learned parameters for the organ-gating classifier may be used in Step S266 and S268 to learn additional neural network parameters for MELD. Step S266 is to perform joint training using the plurality of training datasets to generate parameters for feature extraction layers and fully-connected layers of the lesion detection classifiers. S268 is to train last layers of the lesion detection classifiers to generate a plurality of dataset experts, each dataset expert corresponding to one of the training datasets.

Due to semantic and domain differences, combining multiple datasets may not be straightforward. For example, single-type datasets may lack annotations of other types. For instance, enlarged lymph nodes often exist but are not annotated in LUNA and LiTS. Furthermore, some lesions in single-type datasets may not be considered as significant enough lesions in universal datasets such as DeepLesion. For example, some small and subtle tumors in LiTS may not be annotated in DeepLesion. Thus, there may exist differing definitions of lesions in different datasets. Finally, the image appearances may also be not identical in different datasets, which may be caused by contrast phase differences, imaging quality, and other factors. In order to address these difficulties, a multi-task approach may be used to fuse datasets at the feature-level. In certain embodiments, the different training datasets may share a same 2.5D feature extractor and fully connected layers in the lesion detection classifiers (step S266). The splitting for different datasets may be configured at the last layer of each lesion detection classifier (step 268). For example, suppose D training datasets are used, each lesion detection classifier may output D detection scores to match each dataset's semantics, each detection score corresponding to a specific training dataset.

In certain embodiments, each dataset may have its own RPN and bounding-box regression layers. During inference, multiple groups of bounding boxes may be predicted. Using this approach, the plurality of datasets may share backbone features, which is beneficial especially for small datasets, while their domain and semantic differences will not be confounding.

In certain embodiments, during training, every lesion proposal may go through all M+1 lesion detection classifiers to calculate detection scores $s_0, s_1, \ldots s_M$ and cross-entropy losses $L_0, \ldots, L_M$. The overall loss may be calculated $L = \Sigma_{i=0}^{M} \omega_i L_i$, where the predicted organ weighting parameter $\omega_i$ represents how much of the proposal belongs to organ i. $\omega_0$ should be always 1 as it corresponds to the whole-body classifier. Since the overall loss L takes into account the predicted organ weighting parameters, in certain embodiments, the whole-body classifier may be trained on all proposals while the other organ-specific classifiers may be only trained on positive and negative proposals of a specific organ, forcing them to focus.

It should be noted that the multi-dataset joint training should not be confused with the organ experts, as they are not identical processes. In MELD, different input image may share the same organ-gating classifier and mask classifier. Proposals for every input image may be assigned to the M+1 lesion detection classifiers. In total, MELD predicts (M+1)×D detection scores and M organ-gating weighting coefficients. By contrast, when training data come from a specific dataset d, only the d'th score of each lesion detection classifier will be calculated and fused by the organ weighting coefficients. For example, the liver expert and LN expert may mostly predict zero for LUNA, as lesions in LUNA are only in lungs. Therefore, proposals assigned to the liver and LN experts are mostly negative.

The training process in Steps S262-S268 may be used to jointly learn from universal training datasets, such as DeepLesion, and single-type training datasets such as LUNA, LiTS, and NIH-LN. The training process may use a multi-task approach to fuse datasets at the feature-level and split the datasets at the last layer of each lesion detection classifier. The synergy between universal datasets and single-lesion datasets may be more fully utilized by incorporating both types of datasets for training improve universal lesion detection. The lesion detection classifiers corresponding to the specific datasets may be termed as dataset experts, which may include a plurality of single-type data experts corresponding to the signal-type training datasets and a general data expert corresponding to the universal training dataset.

In certain embodiments of the CAD method provided in the present disclosure, additional steps may be performed to collectively mine lesions from the plurality of training datasets. This process may be termed as Collective Lesion Mining (CLM) because it uses the plurality of datasets in a synergistic manner to overcome certain challenges due to insufficient annotations in the training datasets. The motivation of applying CLM is explained below.

A highly challenging aspect of universal lesion detection is the appearance similarities of certain anatomical structures and lesions. This problem is more serious when the training data is not completely annotated. For example, in the DeepLesion dataset, lesions are only annotated on some of the 2D image slices and there are missing annotations. The 2D images slices having annotations are called key image slices. Only significant lesions are annotated on key image slices in DeepLesion dataset. Along with each key image slice, a sub-volume of neighboring slices was released in DeepLesion but the neighboring slices are not annotated.

Current works typically use key slices of DeepLesion for training, which is biased and may produce false positives when applied on whole 3D image volumes, especially on body parts not well represented in the key slices. A direct solution would be to fully label the dataset. However, annotating medical image datasets is known to be labor-intensive and requires extensive clinical expertise. Knowledge distillation may help to mine missing annotations by training a detector with labeled images and then applying it on unlabeled ones, but the detected proposals may not necessarily be true lesions.

Figure 4:
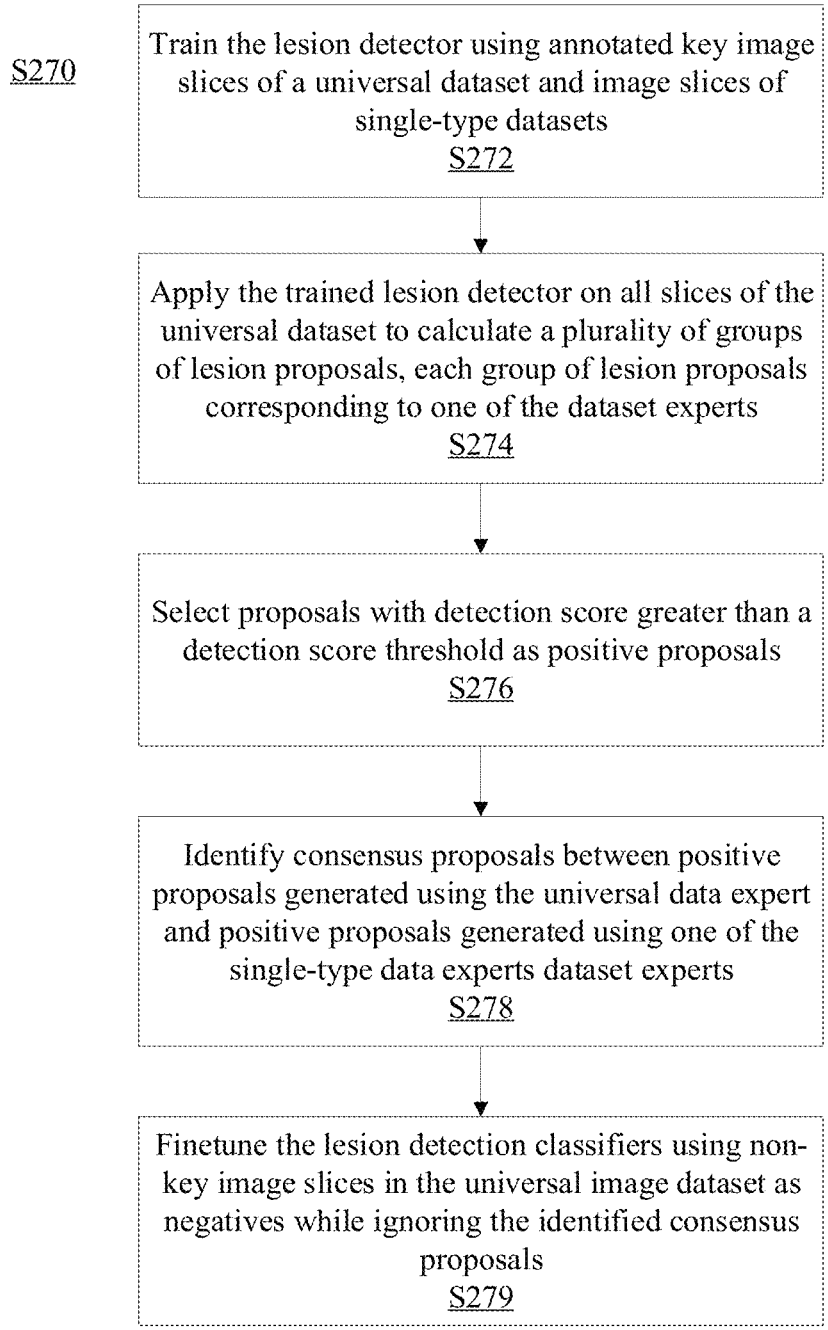
FIG. 4 illustrates a process of the collective lesion mining (CLM) according to certain embodiments of the present disclosure.

In order to address these challenges, the process of CLM may be applied to the training process. The CLM process is based on the intuition that a proposal detected by more than one dataset experts may have a higher probability to be a true lesion. FIG. 4 illustrates the process of the CLM (S270) according to certain embodiments. Certain aspects of the CLM are also illustrated in FIG. 5B. As shown in FIG. 4, the CLM process may include the following steps.

Step S272 of the CLM process is to train the lesion detection classifiers using annotated key image slices of a universal dataset and image slices of single-type datasets. For example, the training datasets may include DeepLesion (universal dataset with 22K annotated key slices), LUNA, LiTS, and NIH-LN. The training process is similar to that described in FIG. 3.

Then, Step S274 is to apply the trained lesion detection classifiers on all slices of the universal dataset to predict a plurality of groups of lesion proposals, each group of lesion proposals corresponding to one of the dataset experts. For example, the plurality of training datasets may be the four datasets of DeepLesion, LUNA, LiTS, and NIH-LN. The dataset experts thus include a universal data expert (i.e., DeepLesion expert) and three single-type data expert (i.e., LUNA expert, LiTS expert, and NIH-LN expert). The trained lesion detection classifier and the corresponding data experts may be applied to all image slices (646K 2D image slices in total) in DeepLesion to generate four groups of lesion proposals corresponding to the four dataset experts.

Step S276 is to select lesion proposals with detection scores greater than a detection score threshold as positive proposals. In certain embodiments, a detection score threshold $\sigma$ may be configured and a proposal with detection score $s > \sigma$ may be kept as positive proposal. The positive proposals are proposals having higher detection scores and thus are deemed as positives according to the corresponding lesion detection classifiers.

Step S278 of the CLM process is to identify consensus proposals between proposals generated using the universal data expert and proposals generated using one of the single-type dataset experts. In certain embodiments, consensus proposals between proposals generated using the universal data expert and proposals generated using one of the single-type dataset experts may be identified according to an intersection over union (IoU) between positive lesion proposals generated by different data experts. Specifically, an IoU threshold $\theta$ may be configured for consensus proposals. If a proposal generated by the universal data expert has an IoU greater than $\theta$ with a proposal corresponding to a single-type data expert, the proposal may be identified as a consensus proposal, signifying that multiple dataset experts reach an agreement on that proposal. For example, if a positive lesion proposal from the DeepLesion expert has an IoU larger than a threshold with a positive lesion proposal of another dataset expert, it may be identified a consensus proposal. The process may be expressed mathematically as: $\forall p_1 \in P_1$, if $\exists p_2 \in P_2$, $IoU(p_1, p_2) > \theta$, and $\forall g \in G$, $IoU(p_1, p_2) < \theta$, then $C \leftarrow C \cup \{p_1\}$, where C is a collection of identified consensus proposals.

Figure 8:
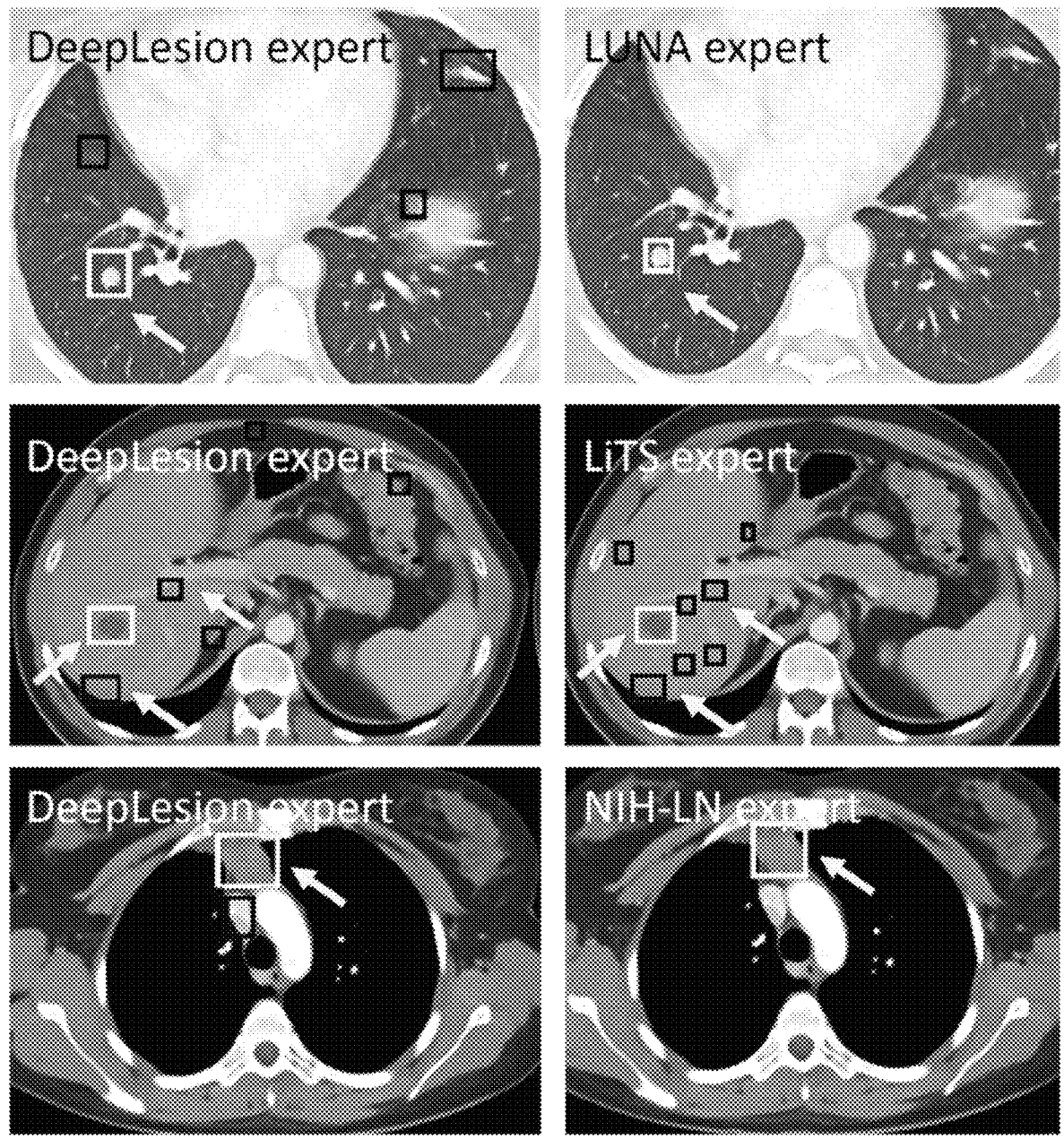
FIG. 8 illustrates examples of consensus proposals from unannotated slices of DeepLesion.

FIG. 8 illustrate examples of consensus proposals from unannotated slices of DeepLesion. The left panel shows three examples of lesion detection results using DeepLesion data expert. A white-line box indicates a true positive (TP) while a dark-line box indicates a false positive (FP). The right panel shows three corresponding diagnosis results using other single-type data experts. As shown in FIG. 8, all TPs are picked up by consensus proposals while most FPs are eliminated by non-consensus proposals. The consensus proposals tend have higher precision than non-consensus ones. Although there are still a few consensus FPs (such as in the second row in FIG. 8), overall, the additional data experts help to reduce FPs of the DeepLesion expert.

Referring back to FIG. 4, Step S279 of the CLM process is to finetune the lesion detection classifiers using non-key image slices in the universal image dataset as negatives while ignoring the identified consensus proposals. The non-key image slices refer to image slices in the dataset that are not annotated.

In certain embodiments of the CAD method, consensus proposals may be regarded as suspicious lesions, thus are not be treated as negatives in training. As an example, the lesion detector may be finetuned by using all slices in the training set of DeepLesion while ignoring the consensus proposals when calculating the cross-entropy losses. Thus, the non-key slices provide additional information of normal tissues for the network to learn. The following algorithm illustrates an example of implementing the CLM process.

In certain embodiments, a subset of non-key slices may be used in a specific training epoch for the finetuning. For example, in each training epoch, all N key-slices and randomly sampled rN non-key slices may be used. When sampling training proposals on each slice, proposals overlapped with consensus proposals are not be sampled, i.e., do not sample p if $\exists p_c \in C$, $IoU(p, p_c) > \theta$.

In certain other embodiments, another process may be applied to address the issue of missing annotations in training data. The process may be termed as missing annotation matching (MAM). In clinical practice, each patient may undergo multiple CT scans (also known as studies) at different time points to monitor their disease progress. Each study typically contains multiple image volumes (also known as series) that are scanned at a same time point but differ in reconstruction filters, contrast phases, and other imaging parameters. A lesion instance may exist across multiple studies and series, but radiologists often do not mark all of them all in their daily work. Besides, a large lesion may span in multiple slices in a volume, but radiologists generally only mark it on the slice where it has the largest cross-sectional size, known as the key slice. These clinical prior knowledge may be utilized to find those missing annotations that belong to the same lesion instance with existing annotations but were not marked by radiologists.

Figure 5:
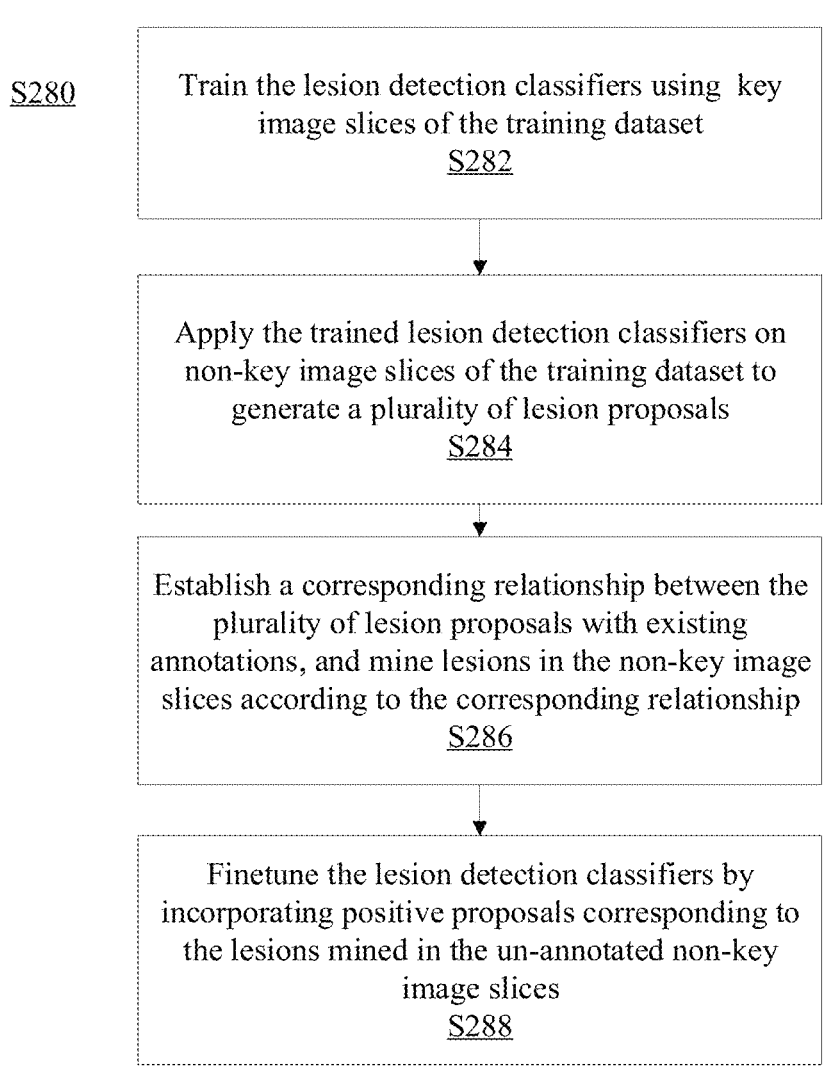
FIG. 5 illustrates a process of the missing annotation matching (MAM) according to certain embodiments of the present disclosure.

As shown in FIG. 5, the MAM process (S280) may include the following steps. Step S282 of the MAM process is to train the lesion detection classifiers using annotated key image slices of the training dataset. The key image slices may be fully annotated image slices in the dataset. For example, the MELD classifier may be trained using the existing annotations on key slices in the training set of DeepLesion having 22K annotated key slices.

Next, Step S284 is to apply the trained lesion detection classifiers on non-key image slices of the training dataset to generate a plurality of lesion proposals. The non-key image slices may be un-annotated and/or partially annotated image slices of the training dataset. For example, in the DeepLesion dataset, after sampling a slice every 5 mm, 1,429K proposals may be obtained from 233K partially-annotated and un-annotated slices, a large extension compared to the 22K key slices.

Next, Step S286 is to establish a corresponding relationship between the plurality of lesion proposals with existing annotations, and mine lesions in non-key image slices in the training dataset. For example, for the DeepLesion dataset, lesion embeddings generated by LesaNet may be used. LesaNet encodes body parts, types, and attributes of lesions in DeepLesion and have proved its efficacy in lesion retrieval. Intuitively, when two embeddings are from a same lesion instance, a distance between the two embeddings should be small. Thus, within each patient, an L2 distance may be calculated between every annotation and every proposal. The pairs of annotation and proposal having L2 distances below a threshold θ may be kept as positive pairs.

Figure 7A:
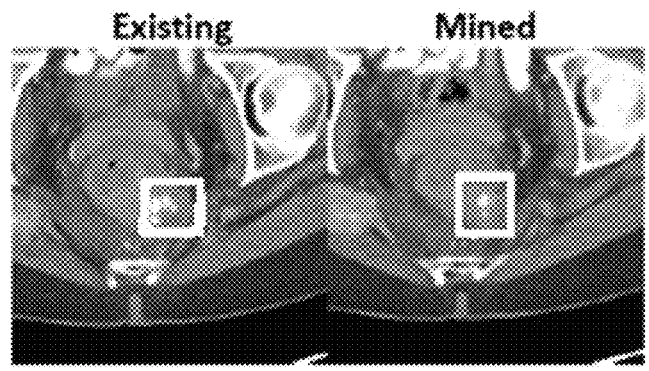
FIG. 7A illustrate an example of matched lesions in DeepLesion for a specific patient.
Figure 7B:
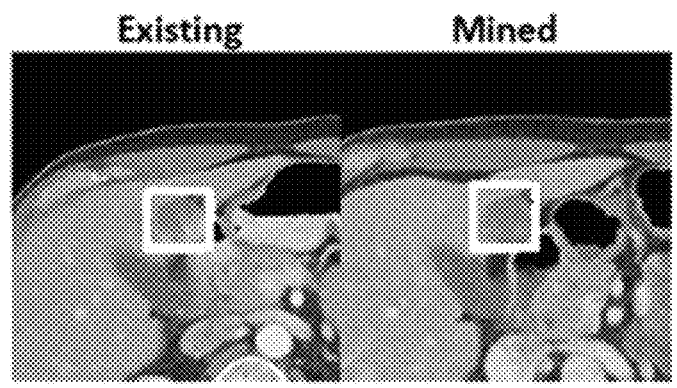
FIG. 7B illustrate another example of matched lesions in DeepLesion for another patient.
Figure 7C:
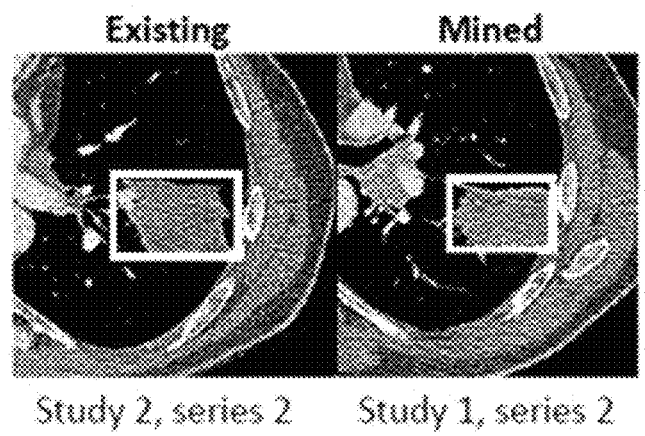
FIG. 7C illustrate another example of matched lesions in DeepLesion for another patient.

FIGS. 7A-7C illustrate examples of matched lesions in DeepLesion. In each drawing, the lesion marked by the white bounding box on the left panel is an existing annotation and the marked lesion in the right panel is a matched missing annotation in another study/series/slice of the same patient. The embedding distances are also shown for the three pairs of matched lesions. As demonstrated by the examples of FIGS. 7A-7C, the mined lesions may generally have the same instances as annotated ones. Occasionally, however, they may be different instances with similar semantic attributes, e.g., two liver metastatic tumors. It is also noted that the mined lesions may have similar but not identical appearances with annotated lesions, since the mined lesions may correspond to a different time point, a different reconstruction kernel, a different slice position, and so on. Thus, the mined lesions may still provide valuable new information when they are used in training.

Referring back to FIG. 5, Step S288 of the MAM process is to finetune the lesion detection classifiers by incorporating positive proposals corresponding to the lesions mined in the un-annotated non-key image slices. In certain embodiments, the mined lesion may be used only in training the lesion detection classifiers but not in training the bounding-box regression classifier, since the mined lesion are detected proposals and the boxes may be inaccurate.

In the following examples, various aspects of the CAD method are implemented using available training datasets. Efficacy of the CAD method is demonstrated by applying the trained lesion detector on various input images.

Figure 9:
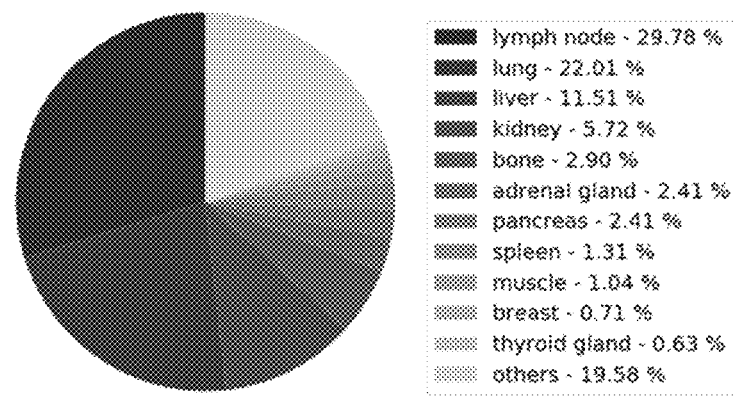
FIG. 9 shows ratios of major organs in which the analyzed lesions belong to according to some embodiments of the present disclosure.
Figure 10:
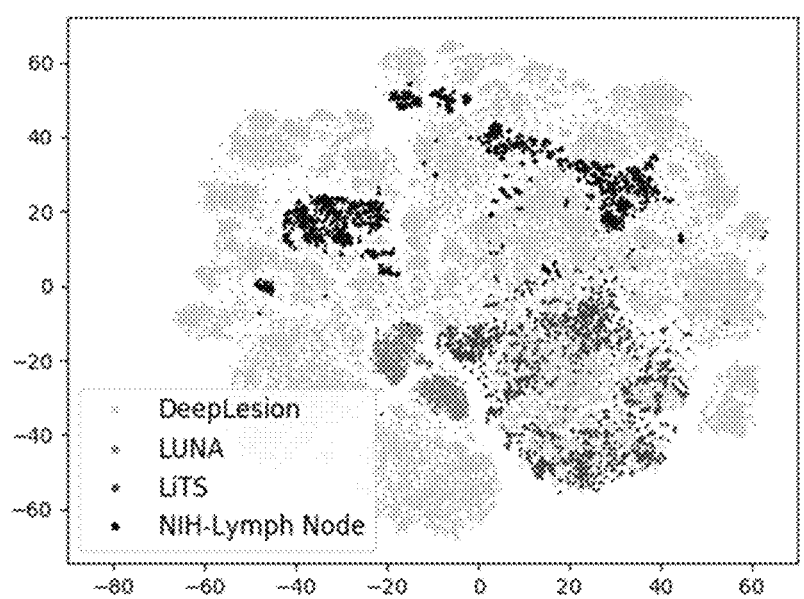
FIG. 10 shows a scatter map of embeddings of lesions in DeepLesion, LUNA, LiTS, and NIH-LN computed by t-SNE according to some embodiments of the present disclosure.

The datasets used for training include DeepLesion, LUNA, LiTS, and NIH-LN. Presently, DeepLesion is the largest dataset for universal lesion detection, containing 32,735 lesions annotated on 32,120 axial CT slices from 10,594 studies of 4,427 patients. It was mined from the National Institutes of Health Clinical Center based on marks annotated by radiologists during their routine work to measure significant image findings. Thus, this dataset closely reflects clinical needs. Based on the lesion tags provided by LesaNet, 17,705 lesions with body part tags are analyzed. FIG. 9 shows ratios of major organs in which the analyzed lesions belong to. As shown in FIG. 9, lymph node (LN), lung, and liver are the most common organs, which are also covered by the single-type datasets. The LUNA (Lung Nodule Analysis) dataset consists of 1,186 lung nodules annotated in 888 CT scans. LiTS (Liver Tumor Segmentation Benchmark) includes 201 CT scans with 0 to 75 tumors annotated per scan. In the examples shown here, 131 scans of the LiTS with released annotations are used. NIH-Lymph Node (NIH-LN) contains 388 mediastinal LNs in 90 CT scans and 595 abdominal LNs in 86 scans. Without loss of generality, these three single-type datasets are used for joint learning with DeepLesion. To observe the distribution of the four datasets, 256-dimensional lesion embeddings from LesaNet are calculated and visualized using t-Distributed Stochastic Neighbor Embedding (t-SNE). FIG. 10 shows a scatter map of embeddings of lesions in DeepLesion, LUNA, LiTS, and NIH-LN computed by t-SNE. As shown in FIG. 10, the single-type datasets lie within subspaces of DeepLesion. NIH-LN is more scattered as lymph nodes exist throughout the body and have diverse contextual appearances.

In order to validate and test the CAD method provided in the present disclosure, a data split of 70%, 15%, and 15% is used for the purposes of training, validation, and test, respectively. The official test set includes only key slices and may contain missing annotations, which may bias the accuracy. Thus, a board-certified radiologist further comprehensively annotated 1,071 sub-volumes chosen from the test set of DeepLesion. Here, the official test set is termed "key-slice test set" and the newly created test set is termed "volumetric test set". In the latter set, there are 1,642 original annotations and 2,023 manually added ones. For LUNA, LiTS, and NIH-LN, 80% of each dataset is randomly chosen for the joint training with DeepLesion.

For implementation, the computation framework is implemented in PyTorch based on the maskrcnn-benchmark project. The backbone of the MELD is a DenseNet-121 initialized with an ImageNet pretrained model. The gating head has two fully connected layers with 512 neurons (FC-512), one FC-3 (for three organs), and a sigmoid function. Each classifier consists of two FC-1024 layers (for the whole-body expert) or two FC-512 layers (for an organ-specific expert), followed by an FC-4 layer for the four dataset experts. Although the CAD method does not limit types of organs in the organ experts, in the following test examples, without loss of generality, lung, liver, and LN are used as organ experts since they are the most common. The neural network layers are randomly initialized. Each mini batch has 4 samples, where each sample consists of 9 axial CT slices for 3D feature fusion. A Rectified Adam (RAdam) process is used to train MELD for 8 epochs with the base learning rate set to 0.0001, then reduced by a factor of 10 after the 4th and 6th epochs. For single-type datasets, all slices that contain lesions and the same number of randomly sampled negative slices (without lesions) are used to train in each epoch. It takes MELD 35 ms to process a slice during inference on a Quadro RTX 6000 GPU.

For the MAM process, an L2 distance threshold is empirically set at θ=0.15. 27K missing annotations are mined from the training set of DeepLesion, in addition to the 23K existing annotations. 100 of the mined lesions are randomly selected and checked, the result shows that 90% of the checked mined lesions are true lesions.

For the CLM process, a detection score threshold is set at σ=0.05, an IoU threshold is set at θ=0.2, and a sampling ratio is set at r=0.5. An average of 5 proposals are generated on each slice and about ⅓ of them are consensus ones. Subsequently, MELD is finetuned from an intermediate checkpoint in the 4th epoch with RAdam for 4 epochs using the same learning rate schedule ($10^{-5}$ to $10^{-6}$). In each finetuning epoch, the original 22K key slices are kept and 10K unlabeled slices are randomly selected to add into the training set. MAM and CLM are used to mine missing annotations and reliable negative region in these 32K slices.

For performance metrics, the free-response receiver operating characteristic (FROC) curve is commonly used in lesion detection methods. On the key-slice test set, sensitivities at 0.5, 1, 2, and 4 false positives (FPs) per slice are calculated. On the volumetric test set, sensitivities at ⅛, ¼, ½, 1, 2, 4, 8 FPs per sub-volume are calculated. The former metric is a proxy showing how many true lesions can be detected on slices known to contain lesions, which can be viewed as the latter metric at more FPs per volume. Note that the 2.5D framework outputs 2D detections per slice, while the latter metric is for 3D detections. Thus, a simple heuristic approach is used to stack 2D boxes to 3D ones. If any 2D cross-section of a stacked 3D box has an IoU >0.5 with a 2D ground-truth box, the 3D box is counted as a TP.

The efficacies of the multi-expert lesion detector (MELD), the missing annotation matching (MAM), and collective lesion mining (CLM) are evaluated by comparing detection sensitivities (%) at different FPs for different combinations of the processes, as shown in Table 1. The previously best-performing method on DeepLesion is Multitask Universal Lesion Analysis Network (MULAN). It is retrained as the baseline method.

As shown in Table 1, MELD outperforms the baseline by 1.7% in average sensitivity at different FP levels. Adding MAM and CLM both significantly boost the accuracy. This means that the missing annotations play a critical role in the detector's performance. MAM adds matched lesions to the positive sample set to make the algorithm learn more about the appearance of different lesions. CLM removes suspicious lesions from the negative sample set to reduce its noise, so that the algorithm can learn the appearance of normal tissues better. Finally, MELD with both MAM and CLM achieved the best result, a relative improvement of 29% compared to the baseline.

For the CLM process, the efficacies of using different single-type datasets to mine suspicious lesions is also investigated. Table 2 lists the detection sensitivity (%) for lesions in different organs. As shown in Table 2, adding a dataset is generally beneficial for lesions in the corresponding organ, confirming the effectiveness of the CLM algorithm to transfer knowledge from single-type datasets.

TABLE 1

Sensitivity (%) at different FPs per sub-volume on the volumetric test set of DeepLesion

| Method | FP@0.125 | 0.25 | 0.5 | 1 | 2 | 4 | 8 | Average |
|---|---|---|---|---|---|---|---|---|
| Baseline | 7.6 | 12.6 | 20.7 | 30.6 | 42.1 | 51.8 | 61.2 | 32.4 |
| MELD | 7.7 | 13.5 | 21.3 | 32.3 | 43.7 | 54.8 | 65.2 | 34.1 |
| MELD + MAM | 12.9 | 20.8 | 29.2 | 39.0 | 49.6 | 58.7 | 67.0 | 39.6 |
| MELD + CLM | 13.5 | 20.2 | 29.5 | 38.8 | 49.4 | 58.5 | 67.3 | 39.6 |
| MELD + MAM + CLM | 16.0 | 22.8 | 32.0 | 41.7 | 51.3 | 60.3 | 68.3 | 41.8 |

DeepLesion

| Single-type dataset | Lung | Liver | Lymph node | Overall |
|---|---|---|---|---|
| LUNA (lung nodules) | 35.5 | 31.7 | 31.7 | 39.4 |
| LiTS (liver tumors) | 34.6 | 39.1 | 33.8 | 40.1 |
| NIH-LN (lymph nodes) | 34.0 | 31.8 | 33.0 | 39.6 |
| All | 35.1 | 38.9 | 35.3 | 41.8 |

Figure 11:
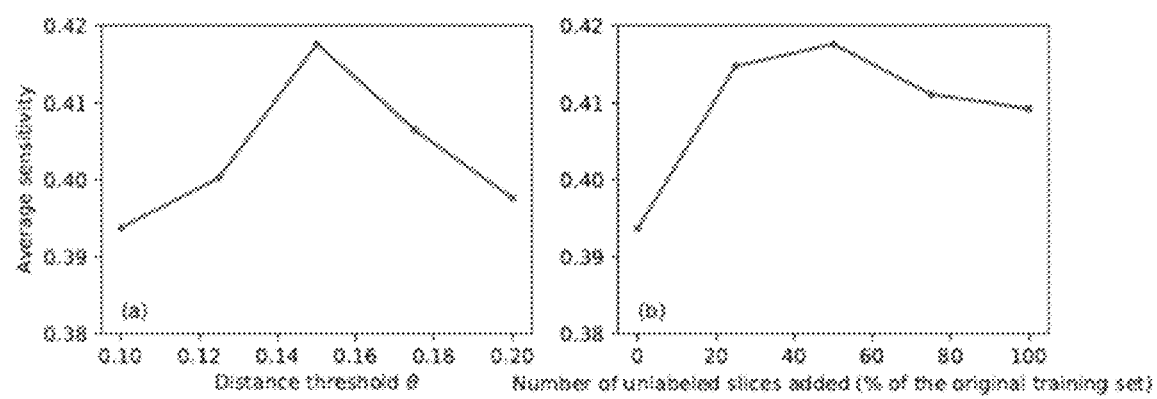
FIG. 11 illustrates results of a parameter study of process of the missing annotation matching (MAM) according to certain embodiments of the present disclosure.

Table 2. Average sensitivity (%) at FP=0.125~8 per sub-volume for different organs on DeepLesion with different training datasets used in CLMThe influence of different parameter values is demonstrated in FIG. 11. The left panel of FIG. 11 illustrates average sensitivity at FP=0.125~8 per sub-volume on DeepLesion as a function of the distance threshold θ. The right panel of FIG. 11 illustrates average sensitivity at FP=0.125~8 per sub-volume on DeepLesion as a function of the ratio between the number of added slices and the original training size (22K key slices). As shown in the left panel of FIG. 11, in MAM, if the distance threshold θ is too small, fewer missing annotations will be matched, providing less new information. If the distance threshold θ is too large, the matched missing annotations may be noisy. The right panel of FIG. 11 shows that adding unlabeled training images may be helpful. With MAM and CLM, the accuracy is already improved on the original training set with no added slices (from MELD's 34.1% in Table 1 to 39.4%). With more unlabeled slices added, MAM and CLM can find positive and negative samples that bring new information, especially for under-represented body parts in the original training set. The accuracy reaches the best when the number of added slices is about half of the size of the original training set. In certain embodiments, the number of added slices is chosen as half of the number of image slices in the original training.

Figure 12:
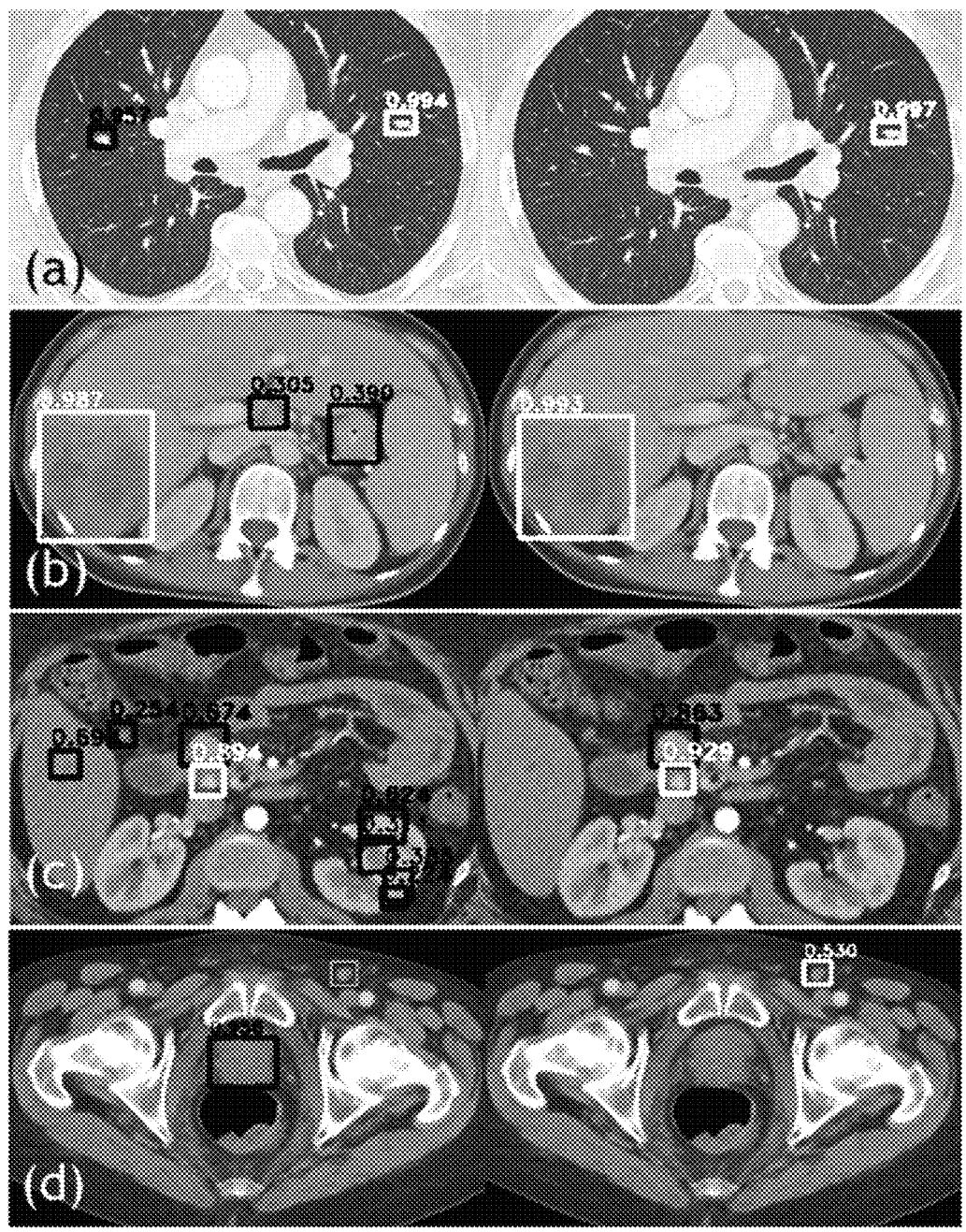
FIG. 12 shows a qualitative comparison of the baseline MULAN and MELD+CLM on the volumetric test set of DeepLesion according to some embodiments of the present disclosure.

FIG. 12 shows a qualitative comparison of the baseline MULAN (left column) and MELD+CLM (right column) on the volumetric test set of DeepLesion. The white-line boxes and dark-line boxes indicate TPs and FPs respectively. The gray-line box shown in the left panel of the last row indicates a ground-truth lesion missed by MULAN. The numbers above boxes are detection scores. As shown in FIG.12, FPs have been reduced notably by MELD+CLM since MELD learns to model normal tissues better when finetuning on non-key slices in DeepLesion. On the other hand, the scores of TPs also increases. This is because CLM excludes many missing annotations when finetuning MELD Without the wrong negative training signals, true lesions can be learned more confidently. Although CLM does not remove all FPs in this example (row (c) of FIG. 12), it significantly reduces FPs and may be further improved by improved organ experts.

A comparison study with existing works is conducted on a partially-labeled key-slice test set. Table 3 shows detection sensitivities (%) at different FPs per slice across several different methods, including a universal lesion detector with pseudo masks and hard negative example mining (ULDor) method, a domain-attentive universal detector method, a volumetric attention method, a multi-view FPN with position-aware attention for deep universal lesion detection (MVP-Net) method, the MULAN method without tags, the MULAN method with tags, the MELD method provided in the present disclosure, and the MELD method with MAM and CLM provided in the present disclosure. As shown in Table 3, MELD outperforms the previous state-of-the-art method, MULAN, either without or with the extra training information of 171 lesion tags. MAM and CLM further boost the accuracy and demonstrate that the mined missing annotations and reliable negative regions are helpful.

TABLE 3

Sensitivity (%) at different FPs per slice on the key-slice test set of DeepLesion based on different methods

| Method | FP@0.5 | 1 | 2 | 4 | Average |
|---|---|---|---|---|---|
| ULDor | 52.9 | 64.8 | 74.8 | 84.4 | 69.2 |
| Domain-attentive universal detector | — | — | — | 87.3 | — |
| Volumetric attention | 69.1 | 77.9 | 83.8 | 87.5 | 79.6 |
| MVP-Net | 73.8 | 81.8 | 87.6 | 91.3 | 83.6 |
| MULAN (without tags) | 76.1 | 82.5 | 87.5 | 90.9 | 84.3 |
| MULAN (with 171 tags) | 76.1 | 83.7 | 88.8 | 92.3 | 85.2 |
| MELD (proposed) | 77.8 | 84.8 | 89.0 | 91.8 | 85.9 |
| MELD + MAM + CLM (proposed) | 78.6 | 85.5 | 89.6 | 92.5 | 86.6 |

Figure 13:
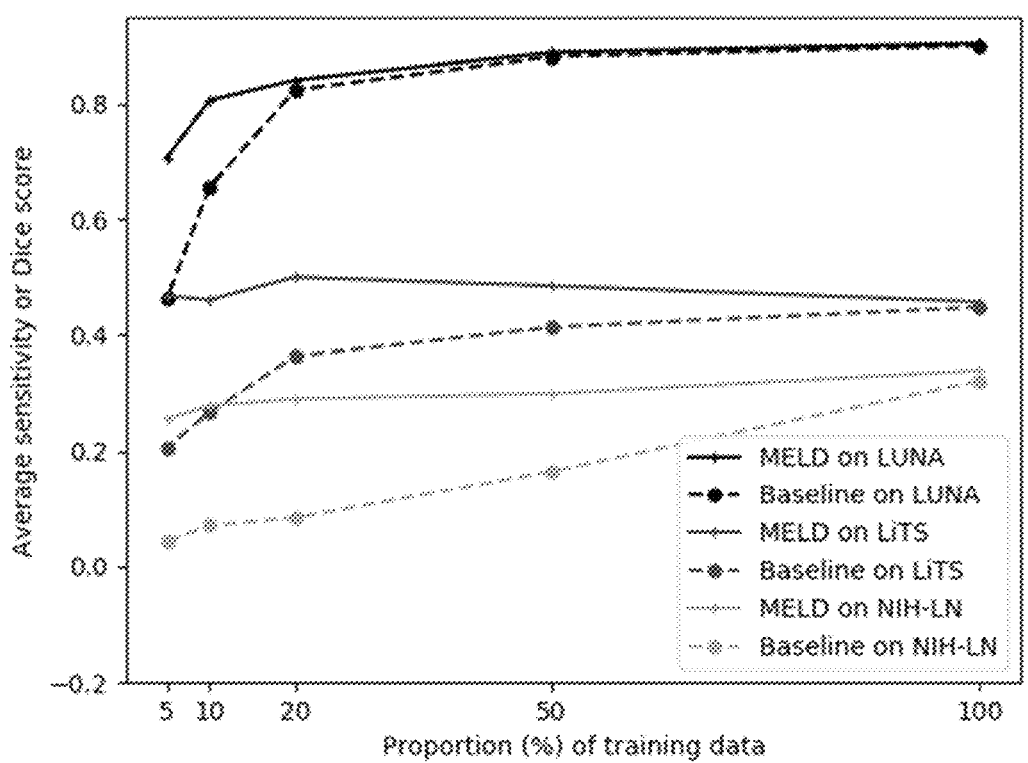
FIG. 13 shows a comparison of MULAN and MELD with different proportions of training data according to some embodiments of the present disclosure.

The joint training strategy in MELD may improve the baseline not only on DeepLesion, but also on single-type datasets, especially when the number of training samples is small. In certain tests, DeepLesion is combined with a proportion of training volumes from the single-type datasets to train MELD For comparison, the baseline is trained with one single-type dataset each time of the same training size. Evaluation is made on the validation set (20% of each dataset). FIG. 13 shows comparison of the baseline and MELD with different proportions of training data in the single-type datasets. On LUNA, an average sensitivity at ⅛~8 FPs per volume is achieved. On LiTS and NIH-LN which have ground-truth masks, Dice score is achieved. As illustrated by FIG. 13, that MELD always outperforms the baseline on the three single-type datasets MELD' s superiority is more evident when the number of training data is getting smaller. This is because DeepLesion contains lesions in a variety of organs, so it can help the single-type datasets learn effective features in the network backbone and organ heads. It is especially useful in medical image analysis where training data is often limited. It also indicates that the network has the capacity to learn different lesion types in multiple datasets at the same time. Among the three single-type datasets, lung nodules have relatively distinct appearance, thus are easier to learn. Besides, LUNA has the more training data, so the superiority of MELD is smaller. Some liver tumors have clear separation with normal tissues, while others can be subtle, making it a harder task. Lymph nodes exist throughout the body and are sometimes hard to be discriminated from the surrounding vessels, muscles, and other organs, leading to the lowest accuracy.

Figure 14:
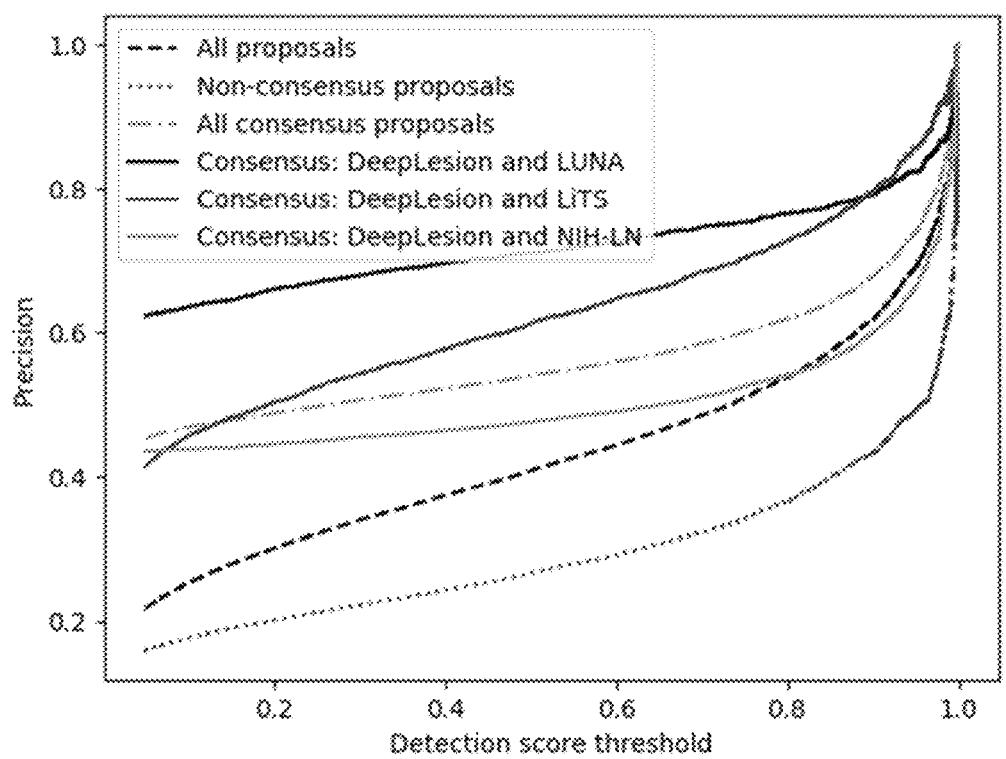
FIG. 14 shows precision of consensus proposals above different detection score thresholds on the volumetric test set of DeepLesion according to some embodiments of the present disclosure.

FIG. 14 shows precision of consensus proposals above different detection score thresholds on the volumetric test set of DeepLesion. FIG. 14 confirms that the consensus proposals used in CLM have much better precision than other proposals, so it is safer to regard them as suspicious lesions.

The present disclosure provides a device and a method for improved universal lesion detection in medical images. The multi-expert lesion detector (MELD) stratifies classifiers based on organs and leveraged the synergy of multiple lesion datasets. The missing annotation matching (MAM) process leverages medical knowledge to find missing annotations with embedding matching. The collective lesion mining (CLM) strategy finds consensus proposals and treats them as suspicious missing annotations during finetuning. Detection results are significantly improved on both universal and single-type lesion datasets. MELD can also be applied in other problems with generalist and specialist datasets. CLM is useful to deal with datasets with imperfect labels.

The method and apparatus provided in the present disclosure according to the embodiments are described in detail above. The principles and implementation manners provided in the present disclosure are described herein by using specific examples. The description of the above embodiments is only used to help understand the method provided in the present disclosure. At the same time, a person skilled in the art will make changes the specific embodiments and the application scope according to the idea provided in the present disclosure. In summary, the contents of the present specification should not be construed as limiting the present disclosure.

The present disclosure contains material that is subject to copyright protection. The copyright is the property of the copyright holder. The copyright holder has no objection to the reproduction of patent documents or patent disclosure in the official records and files of the Patent and Trademark Office.

What is claimed is:

1. A method for performing a computer-aided diagnosis (CAD), comprising:
   receiving a medical image;
   processing the medical image to predict lesion proposals and generating cropped feature maps corresponding to the lesion proposals;
   for each lesion proposal, applying a plurality of lesion detection classifiers to generate a plurality of lesion detection scores, the plurality of lesion detection classifiers including a whole-body classifier and one or more organ-specific classifiers;
   for each lesion proposal, applying an organ-gating classifier to generate a plurality of weighting coefficients corresponding to the plurality of lesion detection classifiers; and
   for each lesion proposal, performing weight gating on the plurality of lesion detection scores with the plurality of weighting coefficients to generate a comprehensive lesion detection score.

2. The method according to claim 1, wherein processing the medical image to predict the lesion proposals and generating cropped feature maps comprise:
   processing the medical image with a 2.5-dimensional (2.5D) feature pyramid network (FPN) to generate a feature map;
   processing the generated feature map with a region proposal network (RPN) to predict the lesion proposals; and
   for each lesion proposal, applying a region-of-interest alignment (RoIAlign) layer to generate a cropped feature map corresponding to the lesion proposal.

3. The method according to claim 1, wherein the lesion proposals include bounding boxes marking locations and spans of predicted lesions.

4. The method according to claim 3, further comprising:
   applying a mask classifier to predict segmentation masks for the lesion proposals; and
   applying bounding-box regression on the whole-body lesion classifier to refine the bounding boxes of the lesion proposals.

5. The method according to claim 1, wherein the organ-specific classifiers include one or more of:
   a classifier for detecting liver lesions;
   a classifier for detecting lung lesions; and
   a classifier for detecting lymph node lesions.

6. The method according to claim 1, further comprising:
   receiving training images from a plurality of training datasets;
   training the organ-gating classifier using the training images and corresponding lesion annotations;

performing joint training using the plurality of training datasets to generate parameters for feature extraction layers and connected layers of the lesion detection classifiers; and
training last layers of the lesion detection classifiers to generate a plurality of dataset experts, each dataset expert corresponding to one of the training datasets.

7. The method according to claim 6, wherein:
the plurality of training datasets include a universal image dataset and one or more single-type image datasets, the universal image dataset containing annotations for a variety of organ and lesion types, and each single-type image dataset containing annotations for a single type of lesions.

8. The method according to claim 7, wherein the single-type image datasets include one or more of:
a liver lesion image dataset;
a lung lesion image dataset; and
a lymph-node lesion image dataset.

9. The method according to claim 7, further comprising:
training the lesion detection classifiers using annotated key image slices of the universal dataset and image slices of single-type datasets;
applying the trained lesion detection classifiers on all slices of the universal image dataset to predict a plurality of groups of lesion proposals, each group of lesion proposals corresponding to one of the dataset experts;
selecting lesion proposals with detection scores greater than a detection score threshold as positive proposals;
identifying consensus proposals between positive proposals generated using the universal data expert and positive proposals generated using one of the single-type data experts; and
finetuning the lesion detection classifiers using non-key image slices in the universal image dataset as negatives while ignoring the identified consensus proposals.

10. The method according to claim 9, wherein identifying consensus proposals includes:
calculating an intersection over union (IoU) between a first positive proposal generated using the universal data expert and a second positive proposal generated using one of the single-type data experts; and
in response to the calculated IoU being greater than an IoU threshold, identifying the first positive proposal being a consensus proposal.

11. The method according to claim 6, further comprising:
training the lesion detection classifiers using annotated key image slices of one or more of the training datasets;
applying the trained lesion detection classifiers on non-key image slices of the one or more of the training datasets to generate a plurality of lesion proposals, the non-key image slices being un-annotated or partially-annotated image slices;
establishing a corresponding relationship between the plurality of lesion proposals with existing annotations;
mining lesions in the non-key image slices in the one or more of the training datasets according to the corresponding relationship; and
finetuning the lesion detection classifiers by incorporating positive proposals corresponding to the lesions mined in the un-annotated non-key image slices.

12. The method according to claim 11, wherein mining lesions in the non-key image slices includes, for each lesion proposal:
calculating an L2 distance from the lesion proposal to each of the existing annotations within a same patient; and
in response to the L2 distance between the lesion proposal and one of the existing annotations within a same patient being below a distance threshold value, identifying the lesion proposal and the existing annotation as a positive pair, and identifying the lesion proposal as a positive proposal.

13. A device for performing computer-aided diagnosis (CAD) based on a medical image, comprising:
a memory, storing computer-executable instructions; and
a processor, coupled with the memory and, when the computer-executable instructions being executed, configured to:
receive the medical image as an input;
process the medical image to predict lesion proposals and generate cropped feature maps corresponding to the lesion proposals;
for each lesion proposal, apply a plurality of lesion detection classifiers to generate a plurality of lesion detection scores, the lesion detection classifiers including a whole-body classifier and one or more organ-specific classifiers;
for each lesion proposal, apply an organ-gating classifier to generate a plurality of weighting coefficients corresponding to the lesion detection classifiers; and
for each lesion proposal, perform weight gating on the lesion detection scores with the weighting coefficients to generate a comprehensive lesion detection score.

14. The device according to claim 13, wherein the processor is further configured to:
receive training images from a plurality of training datasets;
train the organ-gating classifier using the training images and corresponding lesion annotations;
perform joint training using the plurality of training datasets to generate parameters for feature extraction layers and connected layers of the lesion detection classifiers; and
train last layers of the lesion detection classifiers to generate a plurality of dataset experts, each dataset expert corresponding to one of the training datasets.

15. The device according to claim 14, wherein:
the plurality of training datasets include a universal image dataset and one or more single-type image datasets, the universal image dataset containing annotations for a variety of organ and lesion types, and each single-type image dataset containing annotations for a single type of lesions.

16. The device according to claim 15, wherein the processor is further configured to:
train the lesion detection classifiers using annotated key image slices of the universal dataset and image slices of single-type datasets;
apply the trained lesion detection classifiers on all slices of the universal image dataset to predict a plurality of groups of lesion proposals, each group of lesion proposals corresponding to one of the dataset experts;
select lesion proposals with detection scores greater than a detection score threshold as positive proposals;
identify consensus proposals between positive proposals generated using the universal data expert and positive proposals generated using one of the single-type data experts; and finetune the lesion detection classifiers using non-key image slices in the universal image dataset as negatives while ignoring the identified consensus proposals.

17. The device according to claim 14, wherein the processor is further configured to:
- train the lesion detection classifiers using annotated key image slices of one or more of the training datasets;
- apply the trained lesion detection classifiers on non-key image slices of the one or more of the training datasets to generate a plurality of lesion proposals, the non-key image slices being un-annotated or partially-annotated image slices;
- establish a corresponding relationship between the plurality of lesion proposals with existing annotations;
- mine lesions in the non-key image slices in the one or more of the training datasets according to the corresponding relationship; and
- finetune the lesion detection classifiers by incorporating positive proposals corresponding to the lesions mined in the un-annotated non-key image slices.

18. A non-transitory computer-readable storage medium storing a plurality of instructions, wherein when the plurality of instructions are executed by a processor, cause the processor to:
- receive the medical image as an input;
- process the medical image to predict lesion proposals and generate cropped feature maps corresponding to the lesion proposals;
- for each lesion proposal, apply a plurality of lesion detection classifiers to generate a plurality of lesion detection scores, the lesion detection classifiers including a whole-body classifier and one or more organ-specific classifiers;
- for each lesion proposal, apply an organ-gating classifier to generate a plurality of weighting coefficients corresponding to the lesion detection classifiers;
- for each lesion proposal, perform weight gating on the lesion detection scores with the weighting coefficients to generate a comprehensive lesion detection score;
- receive training images from a plurality of training datasets;
- train the organ-gating classifier using the training images and corresponding lesion annotations;
- perform joint training using the plurality of training datasets to generate parameters for feature extraction layers and connected layers of the lesion detection classifiers; and
- train last layers of the lesion detection classifiers to generate a plurality of dataset experts, each dataset expert corresponding to one of the training datasets.

19. The non-transient computer-readable storage medium according to claim 18, wherein:
- the plurality of training datasets include a universal image dataset and one or more single-type image datasets, the universal image dataset containing annotations for a variety of organ and lesion types, and each single-type image dataset containing annotations for a single type of lesions; and
- the plurality of instructions further cause the processor to:
  - train the lesion detection classifiers using annotated key image slices of the universal dataset and image slices of single-type datasets;
  - apply the trained lesion detection classifiers on all slices of the universal image dataset to predict a plurality of groups of lesion proposals, each group of lesion proposals corresponding to one of the dataset experts;
  - select lesion proposals with detection scores greater than a detection score threshold as positive proposals;
  - identify consensus proposals between positive proposals generated using the universal data expert and positive proposals generated using one of the single-type data experts; and
  - finetune the lesion detection classifiers using non-key image slices in the universal image dataset as negatives while ignoring the identified consensus proposals.

20. The non-transient computer-readable storage medium according to claim 18, wherein the plurality of instructions further cause the processor to:
- train the lesion detection classifiers using annotated key image slices of one or more of the training datasets;
- apply the trained lesion detection classifiers on non-key image slices of the one or more of the training datasets to generate a plurality of lesion proposals, the non-key image slices being un-annotated or partially-annotated image slices;
- establish a corresponding relationship between the plurality of lesion proposals with existing annotations;
- mine lesions in the non-key image slices in the one or more of the training datasets according to the corresponding relationship; and
- finetune the lesion detection classifiers by incorporating positive proposals corresponding to the lesions mined in the un-annotated non-key image slices.

* * * * *